United States Patent [19]
O'Meara et al.

[11] Patent Number: 6,075,603
[45] Date of Patent: Jun. 13, 2000

[54] CONTACTLESS ACOUSTIC SENSING SYSTEM WITH DETECTOR ARRAY SCANNING AND SELF-CALIBRATING

[75] Inventors: Thomas R. O'Meara; David M. Pepper, both of Malibu, Calif.

[73] Assignee: Hughes Electronics Corporation, El Segundo, Calif.

[21] Appl. No.: 08/848,929

[22] Filed: May 1, 1997

[51] Int. Cl.$^7$ ...................................................... G01B 9/02
[52] U.S. Cl. ............................................ 356/358; 356/357
[58] Field of Search ..................................... 356/358, 357, 356/432 T; 73/655, 656, 657

[56] References Cited

U.S. PATENT DOCUMENTS

| | | | |
|---|---|---|---|
| 4,966,459 | 10/1990 | Monchalin | 356/358 |
| 5,131,748 | 7/1992 | Monchalin et al. | 356/349 |
| 5,546,187 | 8/1996 | Pepper et al. | 356/357 |
| 5,684,592 | 11/1997 | Mitchell et al. | 356/357 |

*Primary Examiner*—Robert H Kim
*Assistant Examiner*—Andrew H. Lee
*Attorney, Agent, or Firm*—V. D. Duraiswamy; M. W. Sales

[57] ABSTRACT

A contactless system for imaging an acoustic source within a workpiece directs a preferably annular optical probe beam pattern onto the vibrating workpiece surface, with the vibrationally modulated beam then detected by an array of preferably non-steady-state photo-emf detectors arranged in a similar pattern. The probe beam is scanned over the vibrating surface, either mechanically or through an electronically simulated phased array scheme. Time gating is used to suppress unwanted side-lobes when the individual detector outputs are summed over an appreciable waveband. A self-calibration scheme is also preferably used that provides a quantitative as well as qualitative output. A calibration modulation is imposed on at least one of the probe and reference beams, with the calibration modulation later removed at a post-detector stage and used to normalize the acoustic modulation output. Variations of the self-calibration scheme include reference-beam and time-delay interferometers based upon a calibrating phase modulation, and a photon flux measurement approach based upon a calibrating amplitude modulation.

60 Claims, 11 Drawing Sheets

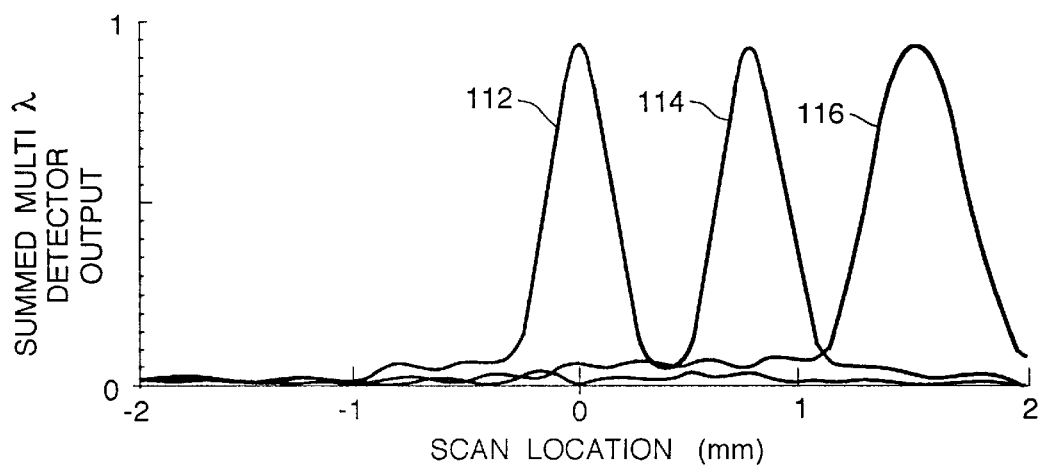
FIG. 12
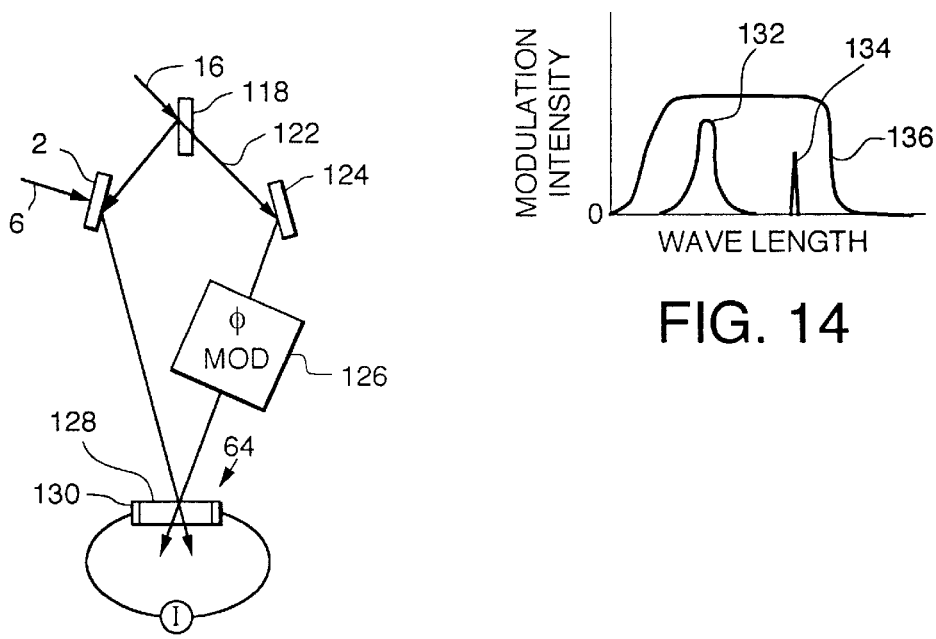
FIG. 14
FIG. 13

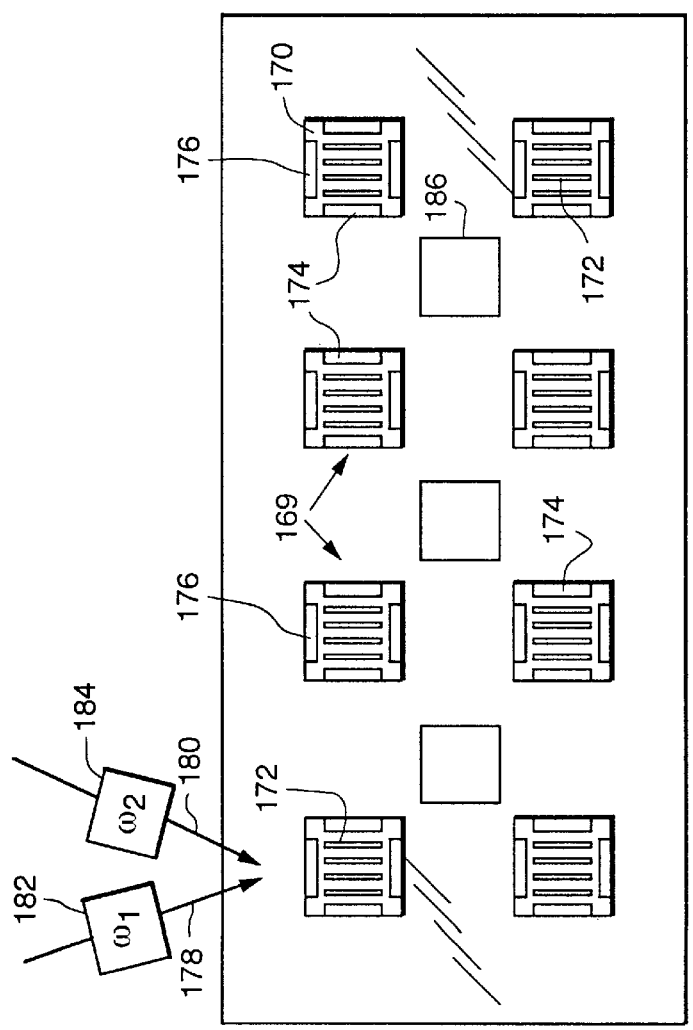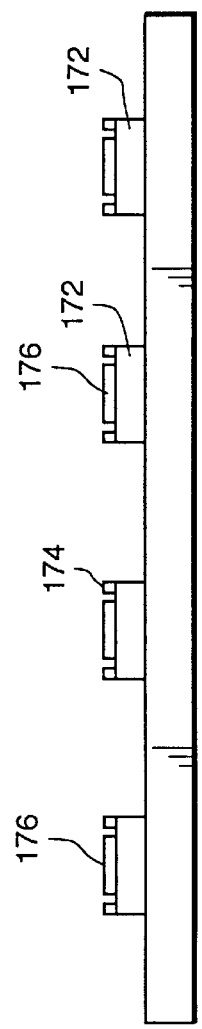
FIG. 17a
FIG. 17b

CONTACTLESS ACOUSTIC SENSING SYSTEM WITH DETECTOR ARRAY SCANNING AND SELF-CALIBRATING

BACKGROUND OF THE INVENTION

1. Field of the Invention

This invention relates to ultrasonic laser-based contactless inspection systems, and more particularly to such systems with two and three-dimensional imaging, electronically controllable steering, focusing and phasing capabilities and self-calibration capabilities.

2. Description of the Related Art

Ultrasonic waves are commonly used to probe a variety of materials, particularly for thickness gauging and flaw detection. The sound waves have usually been generated with a contact piezoelectric transducer (PZT). The launched waves propagate through the material, reflecting from interfaces (in thickness gauging applications) or internal features (in flaw detection applications). The scattered sound propagates back to the surface of the workpiece, causing the surface to vibrate at the ultrasound frequency. This vibration is usually detected with a contact PZT similar to the one used to generate the sound.

Optical detection techniques, such as those described in C. B. Scruby and L. E. Drain, *Laser Ultrasonics, Techniques and Applications*, Adam Hilger, New York (1990), pages 325–350, can be used in place of the piezoelectric transducers to remotely detect the workpiece vibrations. Generally, a laser probe beam is directed onto the workpiece. When the surface vibrates it imparts a phase shift onto the reflected beam. This phase shift is detected with a photodetector after mixing the reflected probe beam with a stable reference beam and measuring the amplitude and frequency or phase of the detector output intensity fluctuations. The reference beam originates from the same laser source as the reflected probe beam, and the output signal from the photodetector or an electronic phase detector corresponds to the surface motion.

One problem with laser detection systems is that extraneous mechanical noise sources can cause additional low frequency vibrations at the surface. These additional vibrations are picked up by the reflected probe beam and reduce the signal-to-noise ratio of the detected signal.

Another problem is low sensitivity. Typically, the workpiece surface that is being probed has a diffusely reflecting or scattering quality. Consequently, the reflected beam is highly aberrated and its wavefront is mismatched with respect to the reference beam. The aberrated reflected beam produces a "speckle" field distribution on the optical detector that is used to detect the optical interference between the reflected and reference beams. The phase relationship between the reflected probe beam and the reference beam is maintained only over a single "speckle" diameter. Consequently, the phase relationship can be set optimally only for light within the speckle area; light within other speckles will have a different and generally nonoptimal phase relationship with the reference beam. The resulting detector signal can thus be thousands of time weaker, due to multiple speckle capture, than would be the case if the surface were a perfect mirror (in which all light would be in a single speckle).

One prior laser-based ultrasonic detection system, described in U.S. Pat. No. 5,131,748 entitled "Broadband Optical Detection of Transient Motion From a Scattering Surface by Two-Wave Mixing in a Photorefractive Crystal", issued Jul. 21, 1992 to Jean-Pierre Monchalin, et al., addresses the wavefront matching problem. In this system the reflected probe beam optically interferes inside a photorefractive crystal with a "pump" beam that is derived from the same laser. The two beams form a refraction grating inside the crystal that diffracts the pump beam in the propagation direction of the probe beam so that the beams overlap and have substantially matching wavefronts when they exit the crystal. However, the grating matches the phases of the diffracted pump beam and the probe beam, which causes the system's sensitivity to the surface vibrations to be very small in the case of a homodyne detection system. To overcome this problem, a second frequency shifted pump beam is superimposed onto the first pump beam, permitting heterodyne detection. The second pump beam is close enough in frequency to the first pump beam to be Bragg matched to the index grating and, therefore, diffracts off this grating. A second index grating is not written by the second pump beam and the probe beam because the crystal cannot respond fast enough to the moving fringe grating produced between the beams (the frequency shift between the beams results in non-stationary fringes). As a result, the second pump beam only diffracts off the first stationary grating (written by the first pump beam and the probe beam), and the relative phase between it and the probe beam is preserved.

Although this technique improves the system's sensitivity, it suffers from many limitations. Although the wavefronts of the probe beam and the diffracted pump beam are matched, they are matched to the aberrated and highly speckled wavefront of the probe beam rather than to the clean wavefront of the pump beam, resulting in a degradation of the coherently detected beam. Second, if the workpiece surface is de-polarizing, the sensitivity of the detector goes down. In addition, if the workpiece surface contains highly contrasting features (for example, pits, rust, spots, etc.), the two-wave mixing amplification may result in non-uniform "print-through" (due to pump depletion), which degrates the system performance. Finally, the Monchalin system does not automatically compensate for extraneous acoustic noise sources which cause additional vibrations at the surface. These spurious noise sources can dominate the signal limit of the desired feature to be detected and, moreover, can lie in the same ultrasonic frequency band, thereby obscuring the sending of the desired signal. Also, a single detection spot will limit the spatial resolution of the system, so the precision mapping of the desired feature's location may not be resolvable. Furthermore, the use of a single detection spot will place a limit on the sensitivity of the diagnostic, since beyond the threshold probe intensity, optical damage to the sample can result.

An alternative interferometric technique for detecting ultrasound uses a "self-referencing" interferometer that produces an output proportional to a temporal difference vibration signal, rather than to the displacement, of the moving workpiece surface. Time-delay interferometry, described in the Scruby et al. book, pages 123–127, is one such technique. In time-delay interferometry the probe beam that is reflected from the workpiece surface is split into two interferometer beams and then recombined at a standard photodetector, with one of the beams time-delayed with respect to the other such as by having it traverse a longer distance. The two beams are collinear when they are recombined at the photodetector, and the light intensity at the photodetector is proportional to the velocity of the workpiece surface. Ideally, the reflected readout beam is interfered with a time-delayed replica of itself and the wavefronts of the two interfering beams are substantially matched. Consequently, a phase shift in one leg of the interferometer is common to all speckles, and all speckles can be detected optimally. Unlike a conventional interferometer, which has a flat frequency response to phase shifts, a time-delay interferometer has a band-pass type of response. The time-delay interferometer suppresses both the low frequency (below ultrasonic frequencies), as well as certain ultrasonic frequency vibrations.

With this type of system, however, the speckles are often so plentiful and small as to not be compatible with each other after one arm of the interferometer has been time-delayed. The time delay is most easily accomplished with a multi-mode fiber, which further increases the number of speckles and scrambles their locations, making speckle registration impossible. Thus, bulky, long-path-length and expensing precision "re-imaging" interferometer such as a Fobery-Perot unit, is employed. (Furthermore, the time delay must be held constant and stabilized to hold the optical beams in quadrature, if homodyne detection is employed. If the path length difference that causes the time delay is not maintained to within a fraction of a wavelength, the sensitivity of a homodyne system will be greatly reduced.) As a result, velocity interferometers must typically employ active stabilization techniques. In industrial environments, the frequency range and amplitude of the noise-induced vibrations reduce the effectiveness of active stabilization techniques.

In pending application Ser. No. 08/404,660, filed Mar. 15, 1995 for "Laser-Ultrasonic Non-Destructive, Non-Contacting Inspection System" by the present inventors and others, a phased-array contactless optical excitation and detection scheme is disclosed in which an array of acoustic waves are generated in the workpiece by a short pulse optical transmitter beam with a beam geometry that is tailored to focus the acoustic waves at an inspection site within the workpiece. The acoustic waves are then detected by reflecting an optical readout beam from a vibrating surface of the workpiece and optically interfering it with a reference beam. The readout beam geometry causes it to detect only those acoustic waves that arrive from the focal inspection site; other acoustic waves are out of phase with each other and cancel. The system employs relatively expensive and complex heterodyne detectors with post-processing electronic tracking hardware to compensate for large amplitude, low-frequency whole-body motions typical in an industrial environment. It uses optical summation for beam formation and thus requires path compensation via photorefractive wavefront compensators, which are relatively slow and introduce occasional signal dropouts.

Another pending application by the present inventors and others, Ser. No. 08/481,673, filed Jun. 7, 1995 for "A System and Method for Detecting Ultrasound Using Time-Delay Interferometry", discloses another contactless system in which an optical probe beam is again reflected and phase modulated by a workpiece surface that is vibrated by ultrasound. A time-delay interferometer optically interferes the phase modulated probe beam reflection with a time-delayed replica of itself to produce interference fringes that move in accordance with the workpiece surface displacement temporal differences. The fringes are detected by a non-steady-state photo-electromotive-force (NSSPEMF) detector that generates an output signal when the frequency of the fringe motion exceeds a given threshold. While this system is relatively insensitive to rough workpiece surfaces, suppresses low frequency noise and provides high sensitivity without the need for active stabilization, the delay lines require long, cumbersome optical fibers to form the beam with attendant input-output coupling loses and power limiting non-linear effects.

NSSPEMF detectors are described in M. P. Petrov et al., "Non-steady-state photo-electromotive-force induced by dynamic gratings in partially compensated photoconductors", Journal of Applied Physics, Vol. 68, No. 5, (1990), pages 2216–2225, and in S. I. Stepanov et al., "Measuring Vibration amplitudes in the picometer range using moving light gratings in photoconductive GaAs:Cr", Optical Letters, Vol. 15, No. 21, (1990), pages 1239–1241. They are able to remotely detect minute ultrasonic vibrations (on the order of picometer to nanometer displacements over a 1–30 MHZ bandpass), while automatically compensating for static or dynamic phase noise below about 10 kHz. However, the output of this type of device does not by itself yield a quantitative measure of the workpiece's ultrasonic response—it reveals only qualitative information such as the shape of the surface displacement as a function of time. To properly interpret, classify and process the output information of an ultrasonic sensor or inspection system, quantitative ultrasonic information such as the absolute value of the surface displacement vs. time should be obtained. The output lens of the sensor is not only proportional to the desired displacement, it is also influenced by typical industrial perturbations such as intensity fluctuations caused, for example, by pits or rust, as well as scattering changes due to variations in surface roughness, which can narrow the field-of-view of the class of sensors. Without such information the sensor's output is of rather limited use, even when a non-rule-based neural network processor is employed to classify the information. Moreover, feedback control of the manufacturing process cannot proceed without correct calibration and interpretation of the data.

SUMMARY OF THE INVENTION

The present invention is a laser-ultrasonic inspection system that is suitable for contactless, in-situ operation with a much higher acoustic resolution than many prior contactless optical readout receivers, provides improved point spread functions, eliminates the requirement for optical path matching, has a better image data processing capability, employs multiple detectors so that the loss of any one detector does not substantially impair the overall system, is capable of integration on a single semiconductor chip and eliminates the need for path compensations via wavefront compensators. Another important feature is an automatic calibration scheme that provides quantitative as well as qualitative information on the workpiece vibrations.

The new system can employ either a mechanical or an electronic scanning mode to locate the ultrasonic source. In a mechanical scanning mode the effective imaging lens has an V F# range which extends over several orders of magnitude, providing a depth of focus extending to nearly the plane of the readout surface, with neither acoustic nor optical adjustments. The electronic scanning imaging mode has a wide field-of-view capability that can approach ±45°. In either mode either a continuum or a set of discrete acoustic illumination wavelengths can be employed, with a significant reduction in acoustic speckle effects, or a single high acoustic frequency can be employed if depth resolution is not required. A single-frame "image" of the surface is also possible, using the array outputs separately (i.e., without summing or combining their outputs into a single signal level).

The self-calibration feature enables each pixel of the sensor to accommodate industrial perturbations, including variations in workpiece reflectivity and laser power changes. Electro-optic or acousto-optic techniques are used to define a reference phase shift (in amplitude and frequency) for each pixel of the detector array. Alternately, a novel electrode configuration enables each NSSPEMF detector element to function as its own photodetector, in addition to functioning as an individual motion sensor. The detector can be calibrated in real-time, on a pixel-by-pixel basis since local features on the surface can possess different reflections relative to other points, and in parallel, so that desired quantified ultrasonic displacement information can be easily extracted independent of the laser intensity and fringe visibility.

The invention is implemented with an array of discrete optical detectors, a probe beam that is directed onto the vibrating surface in a pattern that corresponds to the detector array and from there reflected onto the detector array, a reference beam that is directed onto the detector array at a angle to the probe beam to produce fringe patterns on the detectors that correspond to the surface vibration pattern, and a readout system that uses the discrete detector outputs to produce an array output signal indicative of at least a size and two-dimensional location for the acoustic source relative to the vibrating surface. In the preferred embodiment the readout system includes a signal combiner in the form of an annular conductive ring that combines signals from discrete NSSPEMF detectors arranged in an annular array within the ring. The probe beam is scanned relative to the vibrating surface so that the readout system produces a peak array output when the probe beam is aligned with the acoustic source. When the probe and reference beams include multiple corresponding wavelengths, the readout system combines the signals over the range of wavelengths and includes a temporal peak detector that provides an indication of the acoustic source's depth below the surface.

In another embodiment the probe and reference beams are pulsed and the readout system includes time gates that pass the peak array output signal but reject its side-lobes. The analog detector outputs can also be converted to digital signals, and a computer used to add progressively varying sets of phase shifts to the digital detector outputs to simulate scanning over the vibrating surface and to implement the signal combiner by summing the digital outputs for different sets of phase shifts. The computer can also be programmed to perform the time gate function.

Auto-calibration of detector sensitivity is achieved by modulating at least one of the probe and reference beams with a calibration signal using, for example, a phase modulation process, so that the detector fringe patterns also correspond to the calibration signal modulation, extracting normalization signals from the detector fringe patterns that represent the calibration signal, and using the normalization signals to produce a normalized array output. The calibration modulation signal can be segregated from the vibration modulation on a frequency basis, or alternately both the probe and reference beams can be vibrationally modulated and the reference beam differentiated by a time delay. Another way to differentiate the two beams is to amplitude modulate at least one of the beams at a predetermined frequency, and preferably both of the beams at different respective frequencies. The detector includes two sets of electrodes, one of which responds to the vibrational modulation and the other of which responds to the calibration modulation. The first set is substantially parallel to the fringe pattern, while the second set is capacitively coupled to sense the calibration modulation from the fringe pattern. The two sets of electrodes can be coplanar, with the second set orthogonal to the first set and separated therefrom by an insulating medium. Alternately, the second electrode set can be provided as a transparent electrode above and another electrode below the fringe pattern. With either embodiment a computational element in the readout system algebraically computes the array output based upon the outputs of the various electrodes.

These and further features and advantages of the invention will be apparent to those skilled in the art from the following detailed description, taken together with the accompanying drawings.

BRIEF DESCRIPTION OF THE DRAWINGS

FIG. 12 is a graph of a representative output from the computer simulated scanning of FIG. 11, illustrating three acoustic sources;

FIG. 13 is a block diagram of an embodiment of the invention which employs a self-calibration phase modulation scheme;

FIG. 14 is a graph illustrating the wavelengths of a vibrating surface being imaged, the self-calibration modulation and the detector bandpass for the system of FIG. 13;

FIGS. 17a and 17b are respectively plan and elevation views of another self-calibrating embodiment based upon amplitude modulation of the probe and reference beams together with calibration electrodes;

DETAILED DESCRIPTION OF THE INVENTION

Figures 1, 2:
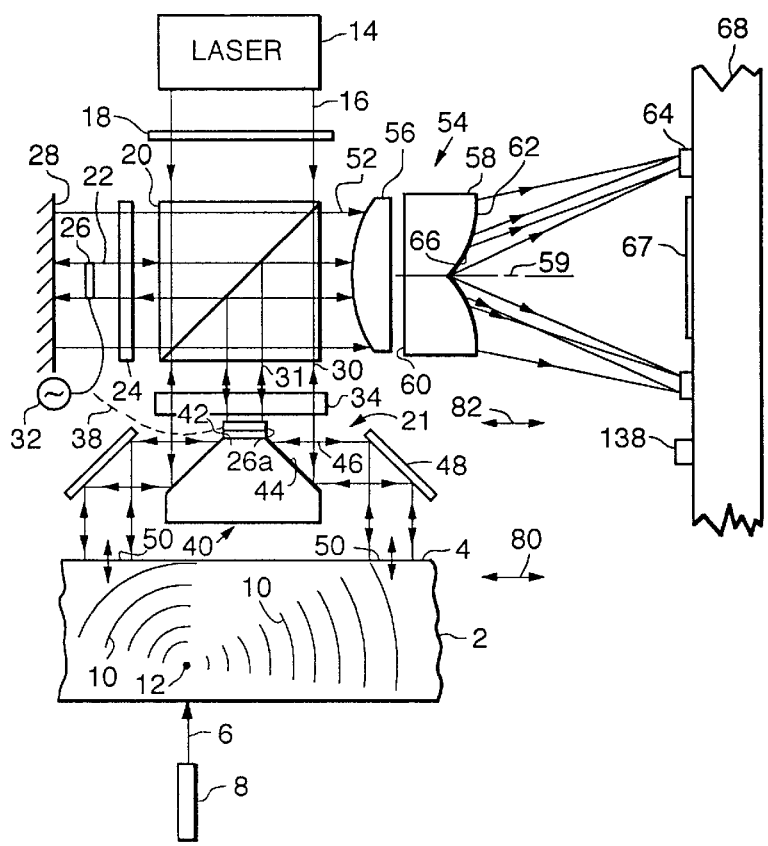
FIG. 1 is a block diagram of a contactless system for locating an acoustic source in accordance with the invention.
FIG. 2 is a simplified elevation view of a preferred detector arrangement used in FIG. 1.

FIG. 1 illustrates a preferred embodiment of the invention in which an in-situ laser-ultrasonic inspection system employs ultrasonic broad-band annular phased arrays for detecting acoustic waves within a workpiece 2 that are manifested by a vibration of the workpiece surface 4. The acoustic ultrasound signals can be self-generated in the workpiece through normal processing, servicing or aging. However, more typically the ultrasound is generated by "pinging" the workpiece with a beam 6 from a laser 8 that is directed to the opposite side of the workpiece from the readout surface 4. The beam 6 would typically contain a set of discrete acoustic wavelengths, or a continuum of wavelengths generated by either a single short pulse or a short burst of several pulses, generated by shock excitation with a short pulse laser. An overview of laser techniques for generating ultrasound is given in C. B. Scruby and L. E. Drain, supra, pages 262–274. The ultrasound waves 10 propagate to the surface 4, causing it to vibrate. If an internal feature 12, such as a weld or crack, is present in the workpiece the amplitude and pattern of the ultrasound waves at the readout surface 4, and thus the surface's vibrational pattern, will be affected. This phenomenon is used to locate and characterize the internal feature 12.

A laser 14 generates an optical probe beam 16 that is directed onto the vibrating surface 4 in a pattern that corresponds to a detector array to be described below. The probe beam diameter is typically about 1–2 mm. It is directed through a quarter-wave plate 18 to a polarizing beam splitter 20, which transmits the beam to an axicon-like optical ring pattern generator 21 from which it is reflected to illuminate the workpiece surface. If a self-calibrating readout system described later in the application is used, the beam splitter 20 can be set up to redirect a portion 22 of the beam through another quarter-wave plate 24 and an electro-optic phase modulator 26 (such as a liquid crystal cell) in the path of the beam's central portion 31 to a mirror 28. From there it is reflected back through the modulator 26 and quarter-wave plate 24 to the beam splitter 20, and from there back to its original path to emerge from the beam splitter as probe beam 30. The electro-optic modulating signal is provided by a modulating voltage source 32.

After passing through another quarter-wave plate 34, the probe beam reaches the optical ring pattern generator apparatus 21. (An alternate location for the electro-optic modulator 26, between quarter-wave plate 34 and the pattern generator 21 which eliminates the need to deflect the beam out of beam splitter 20 toward mirror 28, is indicated by reference numeral 26a and shown energized by modulator source 32 through a dashed line connector 38).

The ring pattern generator 21 has a unique design which includes a frusto conical reflector 40 with an upper reflective surface 42 that receives the central portion 31 of the probe beam, and a reflective conical side surface 44 that receives the annular outer portion 46 of the probe beam and reflects it onto an inclined annular mirror 48, which in turn reflects the outer beam portion onto an annular pattern 50 on the vibrating surface 4. There the outer portion of the probe beam is modulated by the surface vibrations, reflected back up to the annular mirror 48, and from there back onto the outer conical surface of the frusto-conical reflector 40, from which it is reflected up to rejoin the central beam portion 31 in traveling back to the beam splitter 20. From there the acoustically modulated outer beam portion along with the non-acoustically modulated central beam portion is directed as a readout beam 52 onto an optical beam shaper 54, which in turn causes the inner and outer portions of the probe beam to overlap and form interference fringe patterns from which, following detection, the location of acoustic source 12 can be established. The central beam portion 31 acts as a reference beam for the acoustically modulated outer beam portion in forming the fringes.

The beam shaper 54 includes a lens 56 that images the probe beam onto a shaping lens 58 having a central optical axis 59. The input face 60 of the latter lens is flat, while its opposite front face is specially shaped to establish the fringe patterns. Specifically, the outer annular portion 62 of the lens 58 front face receives the outer vibrationally modulated portion of the probe beam and is inclined at a relatively shallow angle to direct the outer beam portion onto an array of detectors 64 (described below) at a first angle which is relatively shallow with respect to a normal to the detectors. The inner portion 66 of the front face for lens 54 receives the non-acoustically modulated central portion of the probe beam. It has a greater angle to the beam axis than does the outer lens surface 62, the exact angle being selected to superimpose the inner beam portion onto the same detectors 64 as the outer beam portion, but at an angle that is sufficiently greater than the outer beam portion so that optical interference fringe patterns are formed on the detectors.

A generalized detector array is shown in FIG. 2. Discrete detectors 64 are arranged in an annular pattern, which is preferably circular but could also be other shapes such as square or elliptical, that matches the illuminated pattern 50 on the vibrating surface 4. In the illustrated embodiment twenty-four detectors are employed in a ring that surrounds a central ground pad 66. All of these elements are preferably formed on an integrated circuit (IC) chip 68 upon which the remainder of the readout circuitry is also fabricated.

The individual detectors are preferably NSSPEMF devices. Each NSSPEMF detector includes a photorefractive-like photoconductive material, preferably a 1 mm thick sample of semi-insulating GaAs:Cr, with a front face that has been polished to optical quality and anti-reflection coated. Although GaAs:Cr is preferred, other photoconductors such as $Bi_{12}SiO_{20}$, CdTe:V or InP:Fe may also be used, which need not possess an electro-optic coefficient, as is the case with conventional P-R media. The wavelength of laser 14 should be chosen to maximize the photoconductor sensitivity. For a GaAs:Cr photoconductor, laser 14 is preferably a GaAs laser that emits light with a wavelength of 900 nm. The lowest detectable frequency of the fringe motion (and therefore the threshold vibration frequency) is determined by the intrinsic response time of the detector's photoconductor and the intensity of the laser light. With GaAs:Cr, surface vibration frequencies greater than 10 kHz will produce a net current flow across the photoconductor. Once the threshold fringe motion frequency is exceeded, the current flow will be constant with frequency until the upper limit bandpass edge is reached.

A matching array of low input capacitance amplifiers 70 is provided for the detector 64 in a surrounding ring. Amplifiers with low noise and a frequency response indicative of the required lowest acoustic frequency are preferably employed. Surrounding the amplifiers is a ring of respective processing networks 72, and around this array is a conductive combiner ring 74. Each detector 64 is connected through a respective amplifier 70 and processing network 72 to the combiner ring 74, which collects and combines the outputs of all the processing networks. In the simplest case, combiner ring 74 develops currents which represent the collection of all the amplified acoustic signals developed by the detectors, and the processing networks are simply through connections. In a more sophisticated version of the invention, discussed below, in which the probe beam is mechanically scanned with respect to the vibrating surface to determine the location of the acoustic source 12, the signals collected by ring 74 are the time-gated analog summation of all of the amplified detector outputs, and the processing network 72 represents the gating electronics. In another version that uses an electronically simulated scanning, the combined signal represents the ensemble of time-gated and analog-to-digital converted detector signals that are time-division multiplexed, via the processing network 72, into a single collection point that functions as and is equivalent to the collector ring 74.

An output pad 76 contacts the combiner ring 74 to provide access to the ring output. It provides a connection point to a computer 78 that is programmed to perform various functions, depending upon the version of the system that is employed. One of these functions is a summation of the vibrational powers sensed by detector 64 over each wavelength, or waveband, of the probe beam as scanning proceeds; as discussed below, the x,y position of the acoustic source can be determined by observing a peak in the summed signal powers at the moment the probe beam aligns with the acoustic source during scanning. With mechanical scanning the computer can also be used to lower the side lobe level of the array output and hence its susceptibility to clutter interference, while in the simulated scanning mode it computes the detector output phase shifts required to image off-axis, and also provides programming information to the individual amplifiers 70 and processors 72, respectively.

The local vibrations induced on workpiece surface 4 by the acoustic waves 10 impart dynamic phase shifts on the corresponding portions of the probe beam, which in turn cause associated radial motions in the interference patterns generated on the detectors that are positioned at the corresponding locations within the readout annulus. As is well known with NSSPEMFs, this fringe motion generates an AC current out of each detector with frequencies that replicate the acoustic vibrational frequencies modulating the probe beam. That is, the amplitude and phase of each spectral component of the acoustic waves arriving at various points on the illuminated ring of the workpiece surface are substantially replicated in the associated detector 64 and amplifier 70 output currents. For example, if the annular detector array is centered directly above an acoustic source or scatter point, all detector fringe patterns move radially in and out in synchronism, and all detector output frequency components are in phase, independent of the depth of the acoustic source below workpiece surface 4; this occurs even if the fringe patterns are not co-aligned. Conversely, if the annular readout portion of the probe beam is not centered over the acoustic source, some portions of the probe beam will detect vibrations that are further away from the source than others, and the detector outputs will therefore be out-of-phase with each other unless a programmable set of delays are distributed to the network array 72 by the computer 78.

After reflection from rough surfaces, the phase modulated reflected optical wave is not spatially homogeneous and the spatial phase variations produce a mottled fringe pattern. However, it has been experimentally demonstrated that the detector output phasing is only weakly degraded by this effect (in contrast to normal coherent detection), and thus no wavefront compensator is required.

The individual detector output signals substantially replicate the surface vibrational motion only above a high pass frequency associated with the particular detectors and below a low pass frequency determined by the internal detector resistance, the external termination resistance and the combined capacitance of the detector 64, the amplifier 70 and the interconnect wiring. Since the detector resistance is typically quite high (on the order of megohms) and the loading resistance cannot be arbitrarily lowered without sacrificing signal-to-noise performance, it is important that the capacitance be held to very low levels (preferably 1 pf or less) to achieve the high frequency response required for good spatial and temporal resolution. Low capacitance is best achieved in integrated amplifier/detector systems, which permit more than an order of magnitude reduction in capacitance as compared to discrete component configurations. Furthermore, the capacitance of the first amplifier stage is important; a source-follower which minimizes the Miller effect input capacitance enhancement of normal high gain amplifiers is therefore preferred.

The location of an acoustic source within the workpiece can be determined through a lateral scanning of the detection system relative to the workpiece, either by moving the workpiece as indicated by arrow 80 in FIG. 1 and holding the probe system stationary, or moving the probe system as indicated by arrow 82 while holding the workpiece stationary. Scanning the readout laser annular pattern over the workpiece surface essentially images an interior acoustic point source centered on the annulus. With the probe beam of all wavelengths centered over the acoustic source, diverging sound waves from the source arrive substantially in phase at the illuminated portions of the vibrating workpiece surface. Consequently, the output currents from the detector amplifiers 70 add constructively at the summation ring 74 to produce a maximum summed signal output. For off-center acoustic sources, the detector fringes essentially move asynchronously and the detected and amplified currents are substantially dephased and sum to lower values.

Figure 3:
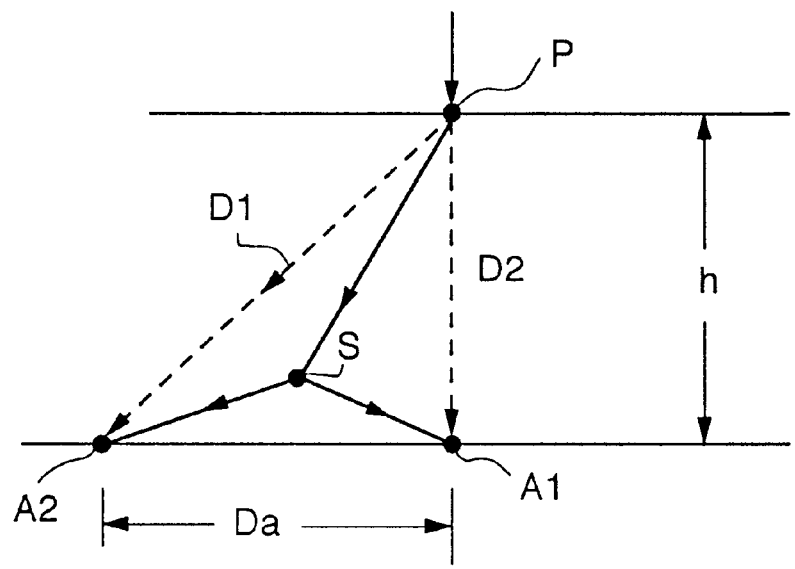
FIG. 3 is a diagram illustrating a preferred laser pinger geometry in which the pinger is located directly above a probe beam annulus on a surface being probed.

With active sources, a generally preferred laser pinger geometry is illustrated in FIG. 3, in which the pinger P is located directly above any point on the annulus central ring. The acoustic ray paths to the scattering site S and from there to the read out annular sites A1 and A2 are illustrated. At the illustrated position of S above the center of the annulus, the scattered rays arrive in temporal coincidence and the readout signals are cophased. This produces a maximum readout signal, which contrasts with the action of the parasitic sound ray paths which arrive at the annulus directly from the pinger site on paths D1 and D2. Such paths are pair-wise equal (in the three dimensional ensemble) but otherwise unequal, and thus the combined signals arrive with unequal times (and phases) and produce strong destructive interference. Thus, the magnitude of the direct path interference is appreciably lowered. Time gating can further reject the direct path signals as discussed below. This pinger geometry presents some problems for sources located just below the read out surface, as discussed below.

Figure 4:
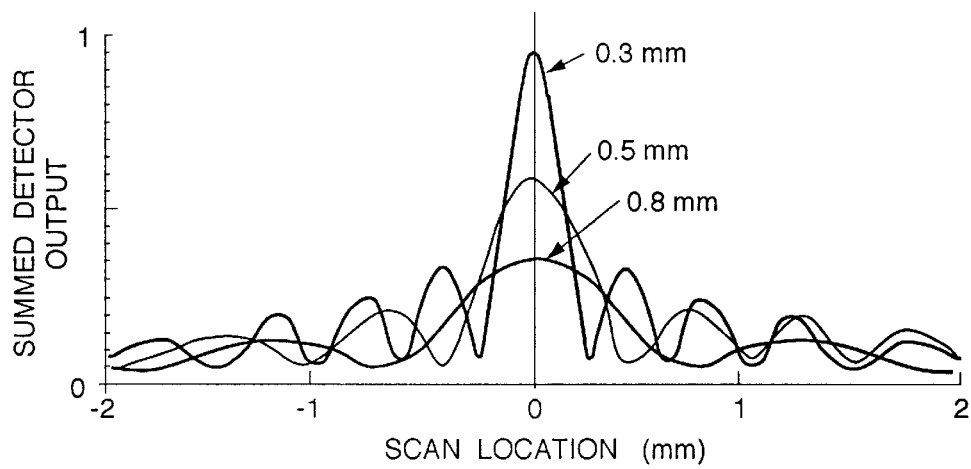
FIG. 4 is a graph of a typical point spread function achieved with the invention in response to scanning over a vibrating surface at three different probe frequencies.

In any linear imaging system, the resolution and contrast are determined by the point spread function (PSF) of the system, which is the array spatial response to a point source (passive systems) or point scatterer (active systems) as it is scanned across the array. Alternatively, the array may be scanned across the point source. A typical point spread function for these arrays is computed for a typical set of parameters in FIG. 4. The PSF shape depends both on the wavelength(s) and the system geometry. In FIG. 4. a broad band source of many wavelengths is assumed and the PSF is effectively averaged over these wavelengths. A broadband acoustic source has the advantage of providing both good temporal resolution and a smoothing of the side-lobe structure produced by a single wavelength acoustic sources exciting an annular array. Broadband sources are typically obtained by sudden internal crack formation (passive sources) or by short pulse pinger lasers (active sources).

The associated summation signal magnitude for an annular probe beam and detector array 2 mm in diameter, imaging an acoustic point source 2 mm below the workpiece surface, is illustrated in FIG. 4 as a function of off-axis scan location. Three point spread patterns are illustrated, for acoustic wavelengths of 0.3 mm, 0.5 mm and 0.8 mm. In the preferred system the "pinging" laser 8 is selected so that multiple acoustic wavelengths are received simultaneously and generate detector and amplifier output signals at each wavelength. By translating the optical readout beam system relative to the vibrating surface, a two-dimensional image of internal absorption or scattering features can be generated. Furthermore, if adequately short acoustic pulses are employed, a three-dimensional image can be generated.

Although the response patterns of FIG. 4 have good resolution for a given wavelength and the assumed geometry, they unfortunately also have high side-lobe levels which make them susceptible to clutter responses and, in many cases, to low contrast imaging. A "white-light" or noncoherent imaging approach can be used to improve the array clutter rejection. This is accomplished by computing the power or intensity of the detector response at each acoustic wavelength and summing the associated point spread functions over all of the wavelengths. Whereas conventional optical systems normally perform such an operation automatically in a noncoherent detector over a continuum of wavelengths, in the present invention it is preferably performed in the post-detection computer 78 over a set of discrete wavelengths or wavelength bands, as indicated by the "power sum" section 84 within the computer.

Figure 5:
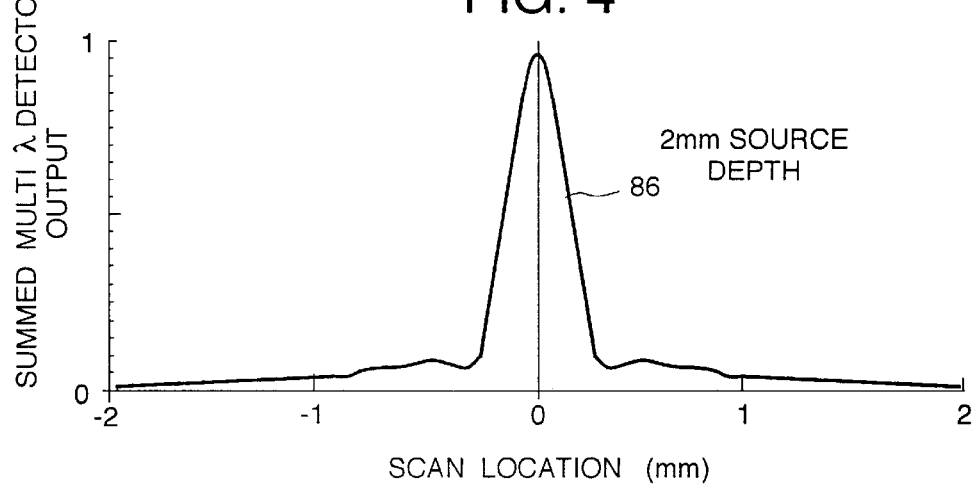
FIG. 5 is a graph illustrating the sum of detector point spread functions over all probe wavelengths.

FIG. 5 illustrates such a "noncoherent", on-axis, point spread function for the same geometry as FIG. 4 and with discrete probe wavelengths of 0.3, 0.35, 0.4, 0.45, 0.5, 0.55 and 0.6 mm. This computation assumes equal intensity "pinging" laser sources having discrete wavelengths at, or wavebands centered upon, the specified wavelengths. The summation image 86 is obtained by summing the squared magnitudes obtained from all of the discrete frequency patterns, such as those illustrated in FIG. 4. The use of multiple wavelengths results in a considerable side-lobe reduction and smoothing which is, in part, a result of the locations of the side-lobe minima being frequency dependent and non-overlapping, as opposed to the maxima which all overlap on the vertical axis. Additional side-lobe suppression is available by employing inverse point spread filtering or inverse convolution processing of the noncoherent image. Such processing is facilitated by the smooth and reduced side-lobe structure of the noncoherent image.

Figure 6:
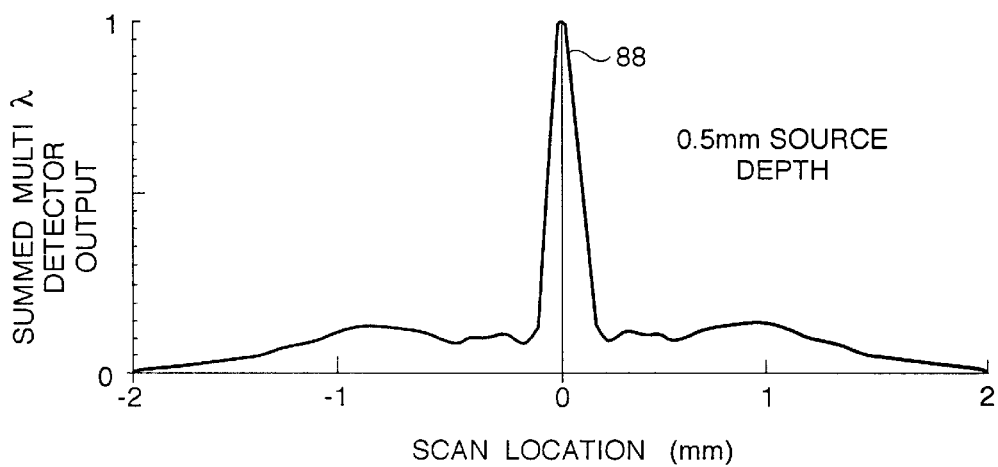
FIGS. 6 and 7 are graphs illustrating the sum of detector point spread functions for acoustic sources that are progressively shallower than that for FIG. 5.
Figure 7:
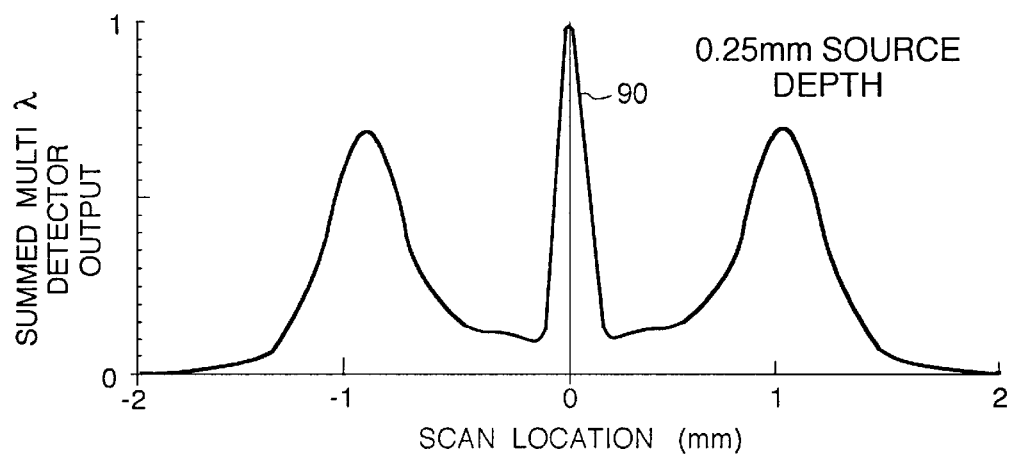

The graph of FIG. 5 is for a 2 mm acoustic source depth. As the source moves closer to the readout surface the multiwavelength (noncoherent) point spread function narrows, as illustrated in FIGS. 6 and 7 for source depths of 0.5 and 0.25 mm, respectively. For the 0.5 mm source depth curve 88 of FIG. 6, the half-power beam width has narrowed to about 0.16 mm, while the side-lobes have increased in magnitude. The beam width is slightly further reduced for the 0.25 mm source depth curve 90 of FIG. 7, but the side-lobe structure greatly increases and peaks for acoustic sources falling under the readout ring. This represents a class of side-lobe response problem which occurs for a very low F# situations, which is not appreciably reduced by the wavelength summation technique discussed above.

Figure 8:
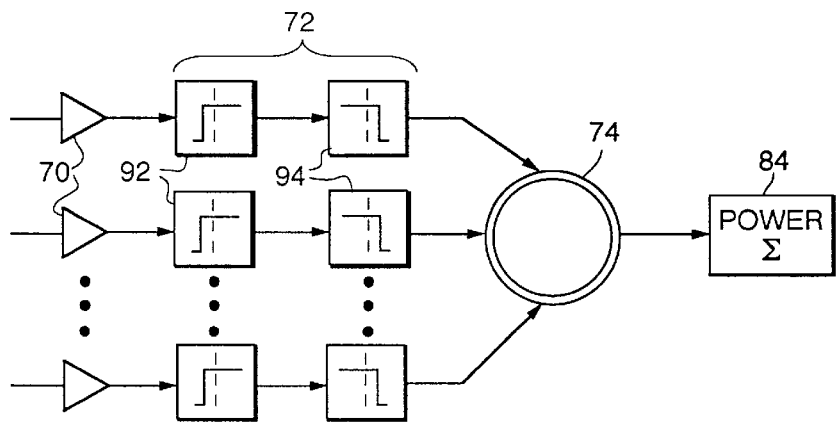
FIGS. 8 and 9 are respectively a block diagram illustrating a time-gated readout used to remove side lobes from the output of FIG. 7, and a graph of the resulting time gated output.

Fortunately, this problem can be substantially eliminated with the use of pulsed acoustic sources, such as using a pulsed laser to "ping" the workpiece, to make it possible to image sources just below the surface. A pulsed source inherently spans many acoustic wavelengths, and is thus not susceptible to clutter responses. For a known source depth and a known acoustic velocity, the expected arrival time of the peak response at each of the detectors is easily estimated (it need not be estimated with high accuracy for the low F# systems where the problem occurs), and the side-lobes arrive at a later time. Time gates can thus be employed to accept the main peak signal and reject the side-lobes. The output portion of such a system is illustrated in FIG. 8, in which the processing networks 72 are implemented with a pair of time gates 92, 94 in series for each detector output, with gate times that are symmetrically displaced about the expected arrival time for their respective detector. Time gates 92 are illustrated as high pass gates with thresholds slightly less than the expected peak arrival time, and time gates 94 as low pass devices with cutoffs slightly beyond the expected peak arrival times. The time-gated outputs from each of the detectors are summed in the combiner ring 74, the output of which goes to the power summing routine 84 within the computer.

Figure 9:
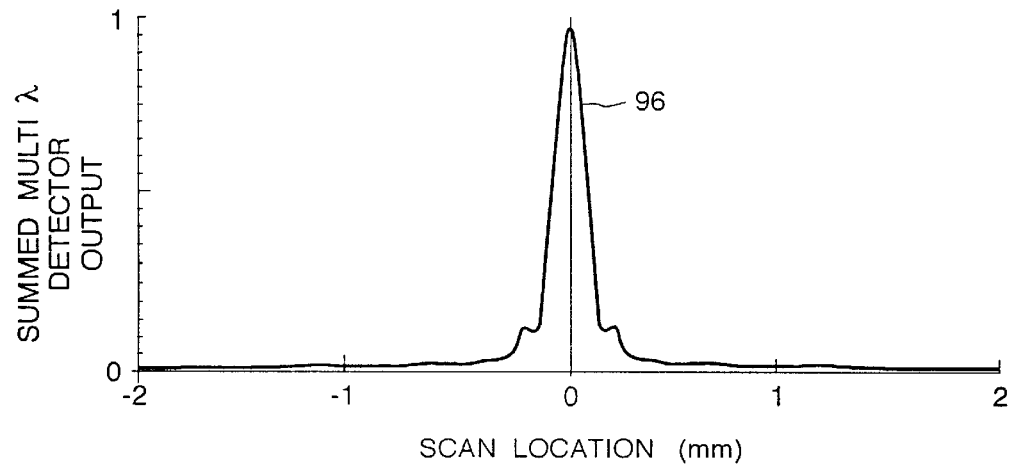

The results of a time-gating correction process for the same conditions as FIG. 7 are illustrated in FIG. 9. In this illustration the expected peak acoustic pulse arrives after 172 nsec from a source depth of 0.25 mm. The time gates are symmetrically displaced about the expected arrival time, at 137 ns and 206 ns respectively. The peak portion of the resulting output curve 96 essentially reproduce the peak of curve 90, but most of the undesirable side-lobes are eliminated.

The time-gating can take place either before or after the detector outputs are summed. However, gating before summation reduces the noise input from the individual detectors. The calculations for the patterns of FIGS. 6, 7 and 9 assume an infinitesimal annular width. Even without this assumption, for widths less than 20% of the highest operational wavelength the impact of width on the pattern shape is very minor.

The dependence of the peak width upon the depth of the acoustic source below the sensed workpiece surface, mentioned above, offers a convenient vehicle to determine the source depth (in the z direction) in addition to its x,y location relative to the surface. The peak width is essentially independent of the vibrational amplitude, and thus the source depth can be established by programming the computer 78 to calculate the width of the peak lobe at half the peak power (or some other convenient portion of the peak power), and to compare it with a programmed reference width to determine the source depth corresponding to the detected width. This operation is indicated by the "½ peak width" section 97 of computer 78 in FIG. 2. For this purpose a profile of source depth versus half-peak width can be established empirically for the type of workpiece in question and programmed into the computer in advance.

There is a class of side-lobe response problem which is not appreciably reduced by broad band operation. This occurs for very low acoustic F# situations, in which the acoustic source is situated just below the read-out surface. This is illustrated by FIG. 7 for a F# 0.25 situation. In addition to a very narrow main lobe, two strong side lobes are generated which correspond to a probe beam position wherein a sector of the read-out annulus falls just above the scatterer or source point. These responses are not a result of array thinning or poor array phasing. Rather they result from a strong local coupling to the proximal array element location, which produces a large 1/R coupling. With active sources, such problems can be alleviated by a time gating technique whose basis is illustrated in FIGS. 3, 9 and 10.

Figure 10:
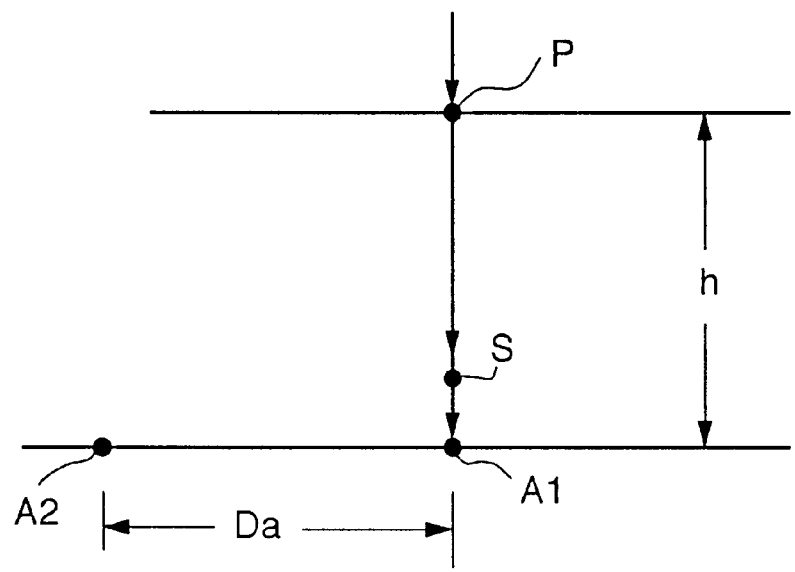
FIG. 10 is a diagram illustrating a laser pinger geometry with pinger and scatter source located just above the edge of the probe beam annulus.

FIG. 10 illustrates a problem geometry—a case corresponding to FIG. 7—with pinger P and scatter source S located just above the annular edge A1. For such cases the total propagation coupling path length is the height of the specimen, h. This path is appreciably shorter than for the (peak response) co-centered scatter and ring positions of FIG. 3. Thus, if the specimen height and sound velocities are known, the spurious response can be eliminated by time gating. The expected time of arrival in the maximum response position is a weak function of the depth of the scatter site, but is much shorter than the FIG. 3 path for most practical cases in which the specimen height does not greatly exceed the annular ring radius, Da/2. Similarly, the other annular cross section point A2 experiences an arrival time which is longer than the arrival time of the maximum response.

An example of an effective point spread function with such time gating is illustrated in FIG. 9 in which uses the same geometrical and wavelength parameters as FIG. 7. However, there exist two locations on the annulus where time gating does not suffice, and thus a co-centered pinger is the preferred location for sources located just below the readout surface.

The mechanical scanning technique described thus far has a useable diffraction-limited beam width which extends over several orders of magnitude in acoustic F#. This depth of focus extends to nearly zero (the plane of the vibrating readout surface) and is obtained without the need for either acoustic or optical adjustments. A simulated scanning technique will now be described which has a wide acoustic field-of-view capability that can approach ±45°. In either mode the preferred acoustic source signals are broad band (one or two octaves) and, as in optical white light imaging, acoustic speckle effects are reduced. However, the system can function with a single high acoustic frequency if depth resolution is not required.

In the simulated scanning mode the computer 78 is programmed to establish a phased array type of operation by introducing phase or time delays that are superimposed onto the outputs of each of the detectors to simulate an acoustic source at an off-axis location, with the delays progressively shifted to simulate a scanning over the workpiece surface. During the entire procedure both the workpiece and the readout structure remain stationary (except for the vibrations of the workpiece surface). True time delays are used for broad band applications, such as "pinging" the workpiece with short laser pulses, to avoid dispersion; for a single frequency source phase shifts can be used instead of true time delays.

Figure 11:
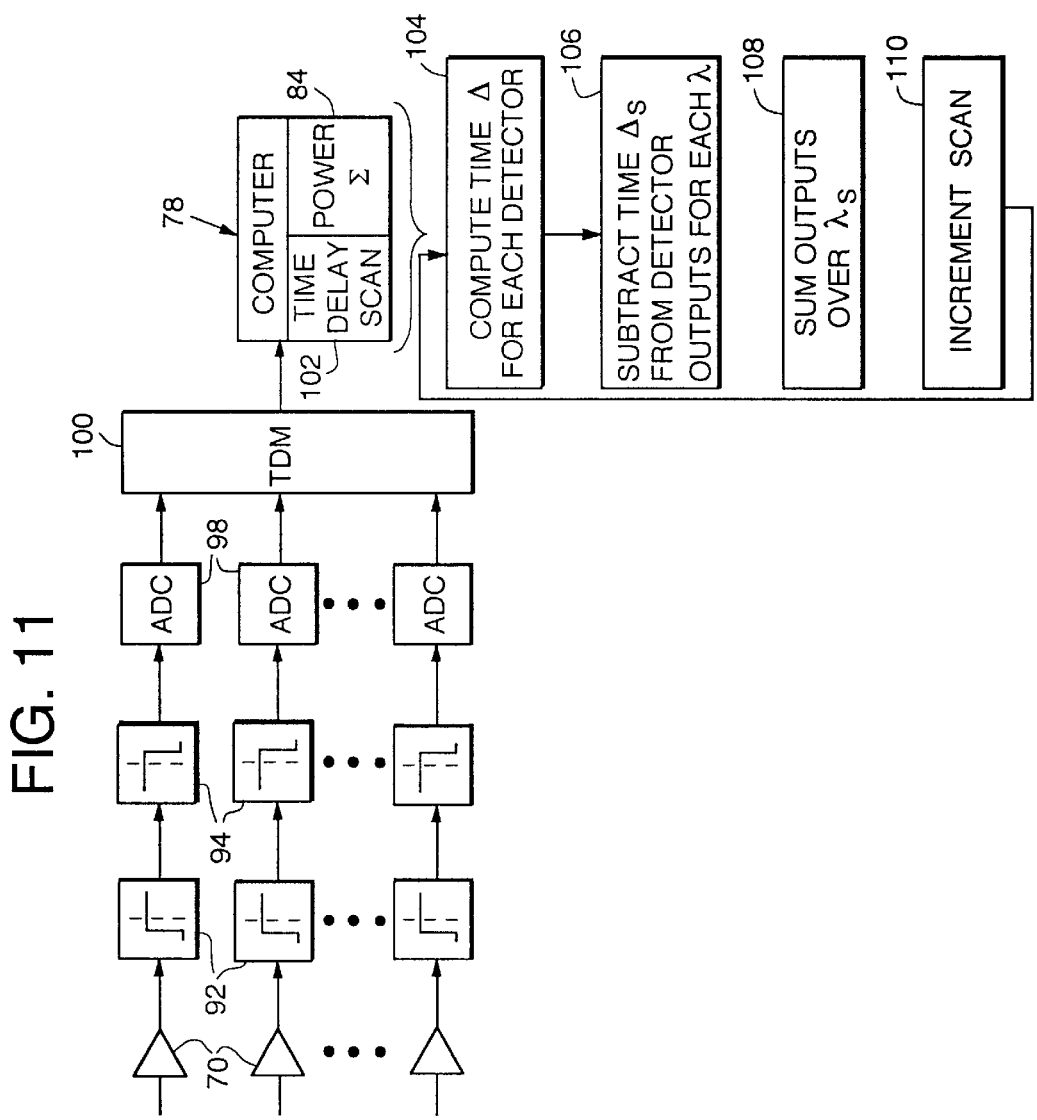
FIG. 11 is a block diagram of a readout circuit used for computer simulated scanning of a vibrating surface.

The readout portion of such a system is illustrated in FIG. 11. The detector output signals are separately converted to digital formats by respective analog-to-digital converters (ADCs) 98 and then processed through a time division multiplexer (TDM) 100 for inputting to the computer 78. Since there is a relatively large dispersion in arrival times from off-axis sources, time gating side-lobe suppression is not as effective in this application. However, a relatively weak time gating by synchronous time gates 92 and 94 can be incorporated into the system in a manner similar to FIG. 8.

The computer 78 is programmed with a time delay scan algorithm 102 that, in conjunction with the power summation algorithm 84, locates acoustic sources within the workpiece through simulated scanning. At one end of the scan, corresponding to a maximum off-axis potential location for the acoustic source, the time delay associated with the acoustic path from the assumed source location to each of the detectors is computed (block 104), and the time delays are substracted from their associated detector outputs for each wavelength (block 106). The delay-compensated detector outputs are then summed over the acoustic readout spectrum (block 108) to obtain the effective power output at the beginning scan location. The algorithm is then incremented to the next location in the scan (block 110) and the process repeated, with the time delay to each detector computed for the new assumed source location (block 104). This process is repeated for each potential source location in the scan, resulting in the generation a synthetic image of the acoustic source.

FIG. 12 illustrates "point-spread" synthetic images of three unresolved, equal strength, wide band acoustic sources which are located respectively at 0, 0.75 and 1.5 mm off-axis at acoustic wavelengths of 0.3, 0.4, 0.5 and 0.6 mm. The images are shown compensated for amplitude fall off; the uncompensated peak current amplitudes for the 0 mm image 112, the 0.75 mm image 114 and the 1.5 mm image 116 were 2.41, 2.22 and 1.79, respectively. This simulation assumed negligible propagation losses. In most situations such losses will cause a more substantial fall off in intensity with increasingly off-axis sources, and such losses need to be estimated and compensated. Also, resolution decreases with increasing off-axis distance, largely because the effective aperture (which is the projected aperture in the propagation direction) substantially decreases. For the 1.5 mm source location, the projected aperture is approximately 1.5 mm.

With the use of time delay corrections rather than phase corrections for the simulated computer scanning, the detector outputs are summed as multiple time signals rather than as discrete frequencies. This greatly speeds the computation, improves the temporal resolution and also improves the ability to incorporate time gating suppression of side-lobes. The major drawback is that a large amount of temporal data from each detector element must be stored.

For large area scans, a combination of both the mechanical and the electronically simulated scanning systems can be employed. The probe beam and workpiece can be mechanically scanned relative to each other in a series of step-and-repeat steps, with simulated scanning performed at each step. Alternately, multiple probe beams and detector arrays could be provided at successive steps along the workpiece, with each beam/detector combination performing a simulated scanning either simultaneously or in sequence. The step distance would preferably be about 1.2–1.5 detector array diameters. Also, instead of "pinging" the workpiece with a laser to excite the acoustic waves, the readout system can be used to detect and locate the source of acoustic signals originating within the workpiece, such as the "creaking" of an airplane wing.

While the various embodiments described so far can be used to locate one or more acoustic sources within the workpiece, they do not yield the absolute amplitude of the acoustic waves and surface vibrations. Such information would be useful for a variety of laser-based ultrasonic, contactless nondestructive testing applications, including weld joints, solder joints, wire bonds, composite materials and various adhesive bonds. The inspection can be performed on an off-line basis (after the processing has been completed), in between processing steps, on-line during the process or as a means to control the process via servo-control and feedback systems.

Two versions of a self-calibrating technique have been developed that can be used to extract the absolute magnitude of the surface vibrations, and thus of the acoustic waves, imposed onto the probe beam by an ultrasonically excited workpiece surface. These new approaches work despite factors that would normally rule out absolute magnitude detection, such as differences in reflectivity from workpiece-to-workpiece, differences in reflectivity from one portion of a workpiece to another, varying surface characteristics which, for example, can locally modify the range of diffuse scattering or specular angles, and changes in laser power.

The first basic scheme, illustrated in FIG. 13 (in which the same reference numbers as in previous figures are used for common elements) imposes a phase modulation signal with a well-defined phase excursion and frequency (which can be at a single frequency for all detector pixels, or spatially programmed in the case of extreme spatial cross talk) on one of the interacting beams which form fringe patterns on the detector 64. For purposes of illustration, assume that the source laser beam 16 is split by a beam splitter 118, with one beam leg 120 reflecting off the workpiece 2 and acquiring its surface acoustic modulation, and the other beam leg 122 directed by a mirror 124 through a phase modulator 126 onto the detector 64 at an angle to the first leg 120 that results in a complex spatial interference fringe pattern on the surface of the PEMF detector material 128. A current is produced by the detector electrodes 130 that includes both the acoustic vibrational modulation and the calibrating phase modulation (assuming both modulations are within the detector's bandwidth). This is illustrated in FIG. 14, in which the acoustic modulation signal 132 is offset in wavelength from the phase modulation signal 134, with both signals within the detector bandwidth 136. The phase modulation signal is used to calibrate the acoustic modulation signal so as to obtain the absolute amplitude of the acoustic modulation.

Given that the response of the NSSPEMF detector is proportional to the product of the two incident beams, it doesn't matter fundamentally which beam carries the calibration phase modulation. Thus, the phase modulator 126 could be imposed upon the same beam leg 120 that acquires the acoustic modulation. Since both beams have small depth-of-modulation, the detected output will merely be proportional to the sum of the modulation signals, with negligible intermodulation products expected.

Figure 15:
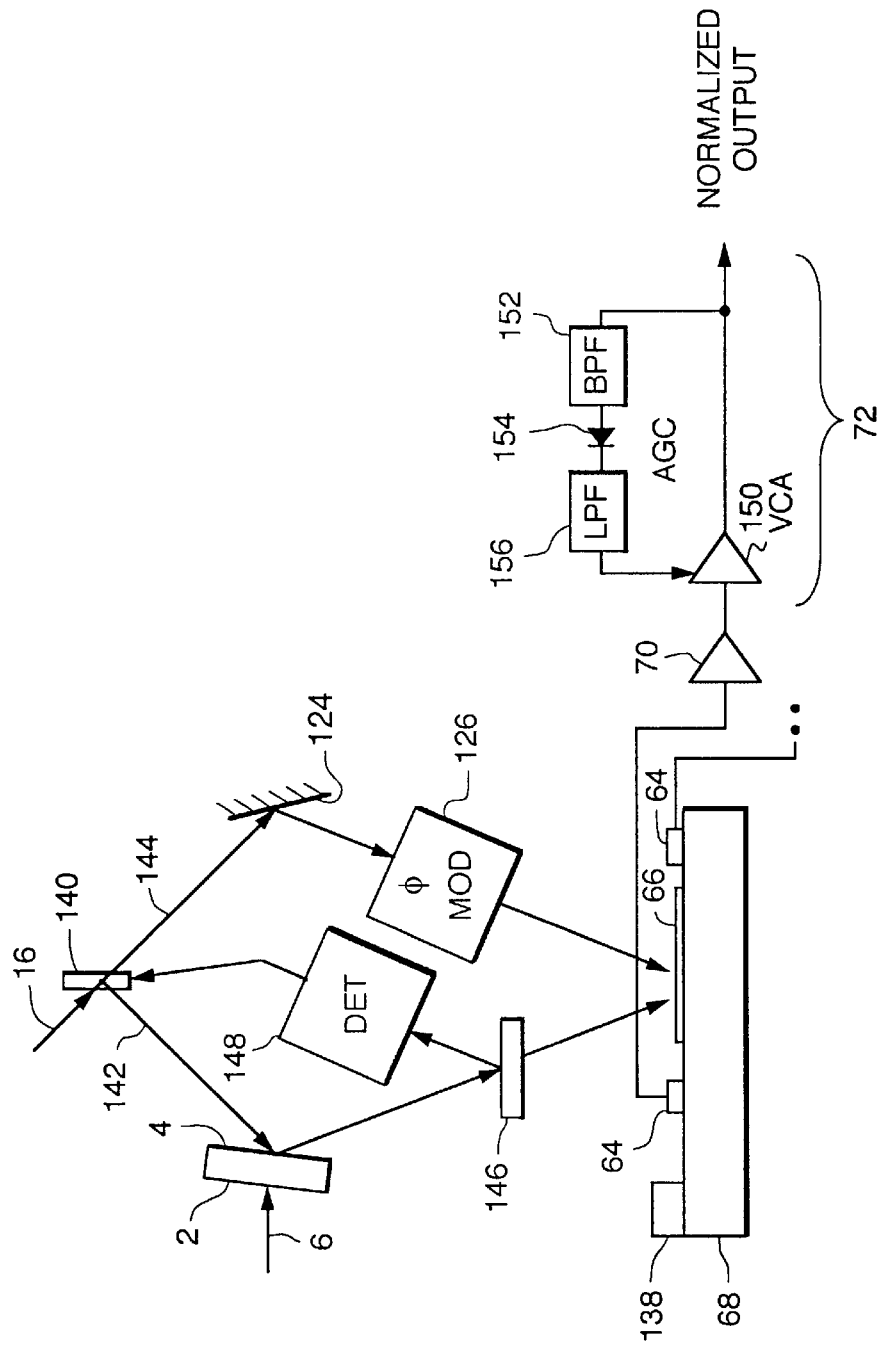
FIG. 15 is a block diagram showing alternate embodiments of a reference-beam interferometer implementation of FIG. 13.
Figure 18:
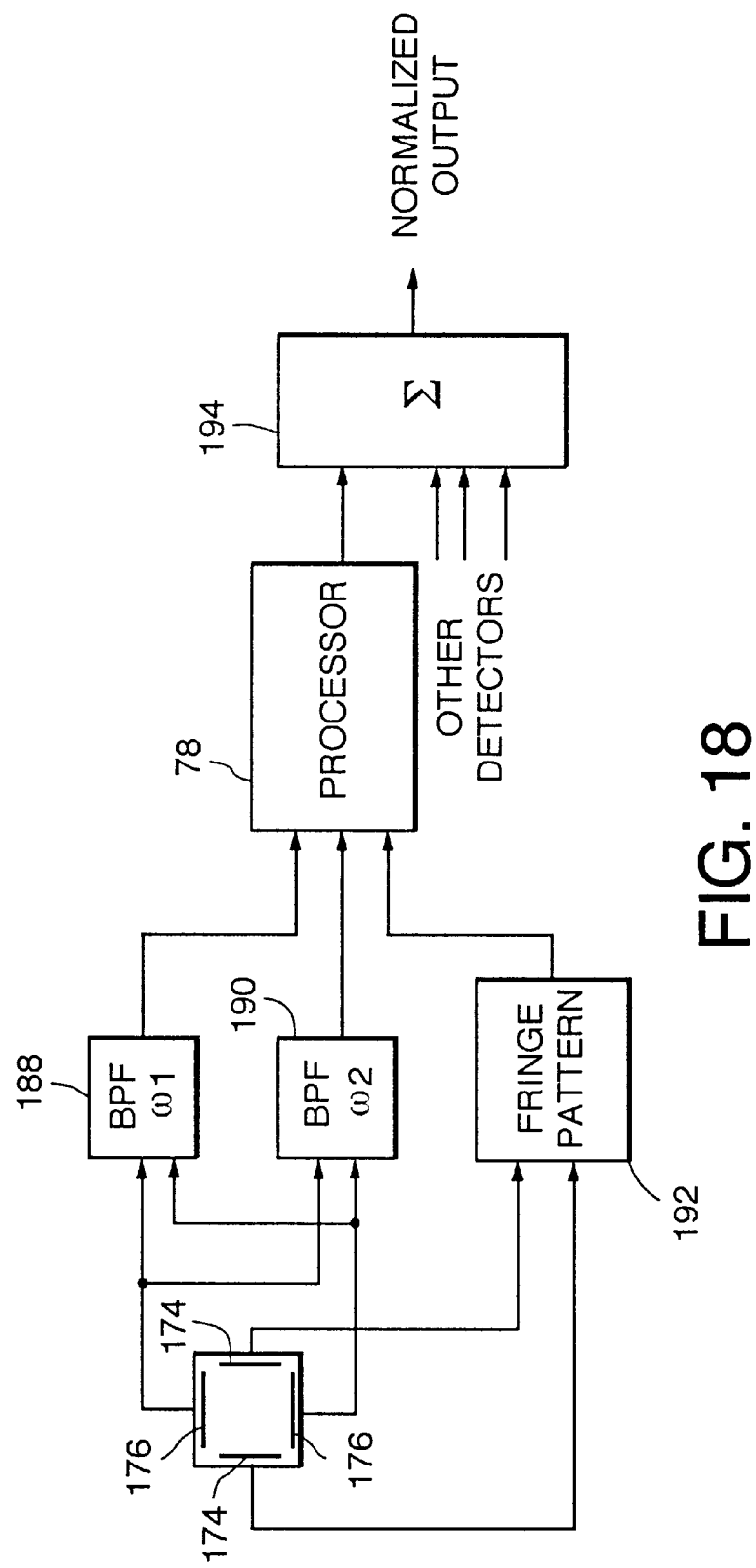
FIG. 18 is a block diagram of output processing circuitry for the detector arrangement of FIGS. 17a and 17b.

Two version of the first basic scheme have been developed, one of which is illustrated in FIG. 15 and employs a reference-beam interferometer in which an acoustically modulated beam 142 is interfered with a phase modulated reference beam 144, and the other of which is illustrated in FIG. 18 and interferes the acoustically modulated source probe beam 16 with a delayed version of itself in a time-delay interferometer. In both cases the detectors 64 respond to a lateral motion of the optical fringe pattern and generate output photocurrents that correlate with the pattern motion and displacement. Also in both cases, the desired calibration phase modulation can be imposed onto one or both of the incident optical beams, or onto the detector itself. The phase modulator 126 can be provided in various conventional forms, such as an electro-optic crystal, a liquid crystal polymer, or an optical fiber wound around a mandrel that is formed from a piezoelectric material and functions as a PZT to modulate the fiber length, and thus the phase of the optical signal transmitted through the fiber, in response to a modulating voltage signal. If the self-calibrating phase modulation is accomplished by a lateral modulating motion of the detector substrate rather than by imposing a phase modulation onto one of the incident beams, this can be implemented with a motion exciter 138 such as a separate PZT exciter using either compression or shear wave excitation, or a surface acoustic wave (SAW) generator using a conventional set of interdigitated electrodes on the detector chip. The central ground pad 66 on the detector chip could also be used as a PZT. Although both the phase modulator 126 and the motion exciter 138 are shown in FIG. 15, in practice one or the other but not both would be used.

Whether the phase modulation is applied to the beam or the detector substrate, a normalized signal which represents the calibration signal is extracted from the detector fringe pattern and used, preferably via a simple automatic gain control (AGC) scheme, to provide a normalized output that represents the absolute amplitude of the workpiece's surface vibrations. The amplitude of the calibration modulation is preferably chosen to be in the range of the anticipated ultrasonic acoustic signal, so that no additional post-processing amplitude filtering is required. The frequency of the calibration signal is conveniently chosen to be outside the bandpass of the anticipated laser-based acoustic signal so that the two signals can be spectrally distinguished with simple filtering.

Spatially modulating the detector itself is a viable alternative to imposing a phase modulation onto one of the beams, since it is the relative motion between the detector and the optical pattern that is the key; either the light or the detectors can shift for a finite photocurrent to be generated. The result is a relative motion of the detector pixels. Such a lateral motion generator can be integrated into a common structure with the detector array, resulting in a monolithic detector package. The required electronic processing, such as filtering, feedback control and AGC discussed below, can be integrated into the same chip on a pixel-by-pixel basis, resulting in a compact, robust, self-calibrating acoustic sensor.

In the illustration of a reference-beam interferometer given in FIG. 15, the probe laser beam 16 is divided by an electro-optically controlled beam splitter 140, normally a polarizing beam splitter, with one beam leg 142 reflected off the vibrating surface of workpiece 2 and the other beam leg 144 reflected off mirror 124 to the phase modulator 126. It has been shown that a unity modulation index optimizes the PEMF output response. The desired ratio-control between the two beam legs can be implemented on either a global average or a detector-by-detector basis, if necessary. A global average can be realized by summing the total flux in the probe beam 142 and feeding back this signal to a simple electro-optic modulator such as beam splitter 140 to balance the beam legs. One way to accomplish this is by placing a weakly reflecting mirror 146 in the path of beam leg 142 to reflect a small portion of that leg to an optical detector 148, the output of which is connected to provide a control signal to beam splitter 140. This establishes a feedback loop which senses the light intensity reflected from the workpiece and directs a greater portion of the probe beam to the workpiece leg 142 if its reflected light is too low (which may result, for example, from a rusty workpiece). Alternately, the light intensity in both legs can be detected, with the beam splitter controlled to equalize the intensity of both legs. Another way to accomplish this global averaging operation is to beam split a portion of the probe beam after reflection (and/or scattering) from the workpiece and direct this beam portion into a single, stand-alone detector (which can be integrated on the detector array chip). In extreme cases a spatial light modulator can be used as part of the feedback loop to control the optical intensity at each detector individually, thereby enhancing the response of all detectors simultaneously and in parallel. This ratioing operation can be implemented on all of the self-calibration embodiments described herein.

The output from each detector 64 is amplified by a respective transimpedence amplifier 70, the output of which is in turn delivered to the processing network 72 which is implemented as an AGC circuit. This consists of a voltage controlled amplifier (VCA) 150 that receives the amplified detector output, a bandpass filter 152 at the output of the VCA that extracts the calibration signal but not the acoustic modulation from the VCA output, a rectifying diode 154 at the bandpass filter output, and a low pass filter 156 that provides a low frequency control signal to the VCA from the diode output. Thus, the calibration modulation is used to calibrate the acoustic modulation signal.

Since the intensity of the imposed calibration modulation is known, and the division of the initial probe beam 16 between the two legs 142 and 144 is also known, the amplitude of the output calibration signal extracted by bandpass filter 152 is also known if the vibrating surface of workpiece 2 has a perfect reflectivity and the power of probe beam 16 remains constant. However, if either the workpiece surface has less than optimum reflectivity or the probe beam power varies, this will affect the fringe patterns developed on the detectors and thus the amplitude of the extracted calibration signal. Such changes in amplitude are compensated, and a normalized detector output is produced, by feeding the actual amplitude of the extracted calibration signal back to the VCA 150 to control its degree of amplification. Any variations in the workpiece reflectivity or probe beam power are manifested as changes in the optical intensity on the detector and fringe visibility of the fringe patterns, which in turn alter the extracted calibration signal so that it acts to self-calibrate the system through the AGC loop.

Figure 16:
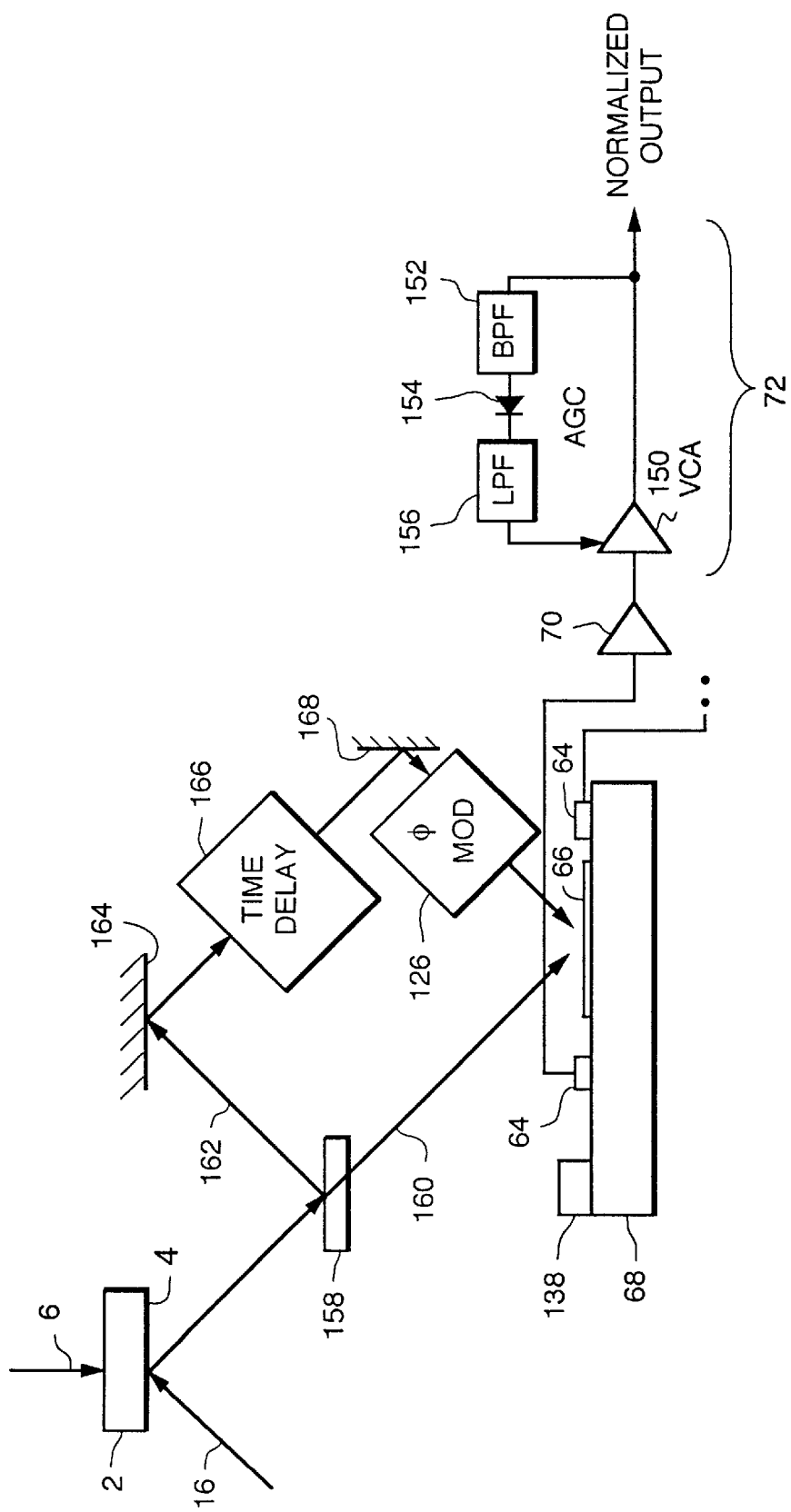
FIG. 16 is a block diagram showing alternate embodiments of a time delay interferometer implementation of FIG. 13.

In the time-delay interferometer implementation of the invention illustrated in FIG. 16, the probe beam 16 is first reflected off the vibrating surface 4 of the workpiece 2. The beam is then split by a beam splitter 158 into two legs 160 and 162. Leg 160 continues directly onto the detector array, while leg 162 is reflected by a mirror 164 through a time delay 166, and then off another mirror 168 and through the same phase modulator 126 as in FIG. 15 to interfere with leg 160 at the detector array. The time delay 166, preferably implemented by an optical fiber delay line, causes leg 162 to have a time varying phase shift with respect to leg 160 at the detector array and to thus form moving interference fringe patterns on the detectors. The detector outputs are processed by the same AGC circuitry as in the reference-beam interferometer embodiment of FIG. 15. As with FIG. 15, the phase modulation can be imposed on the opposite beam leg instead, or the calibrating beam phase modulation could be replaced with a displacement modulation of the detector array.

The calibration signal can be used to normalize out changes in surface reflectivity, scattering, laser power variations in either or both legs, changes in detector response with age, etc. Simple feed-forward, feedback or the illustrated AGC control of FIG. 15 can track such changes. Since the calibration signal is imposed onto all of the detectors, a phased-array system can be realized with very low point-spread function degradation in space or time.

While analog processing circuitry has been illustrated, the processing could also be performed digitally. In that case the detector outputs would be converted to digital formats through ADCs, and the calibration signal extracted with a digital bandpass filter. The acoustic modulation would be extracted with its own digital bandpass filter, with both the digital acoustic and peak digital calibration signals applied to a digital divider which replaces the analog AGC in producing a normalized output that gives the absolute amplitude of the acoustic ultrasound modulation.

In most cases a single calibration modulator will provide the desired reference information. However, in extreme cases or in the case of propagation through multimode optical fibers, frequency flagging of each detector pixel may be required. In these cases each detector would have a separate modulation frequency. Given that the calibrating depth-of-modulation is small (on the order of milliradians), the required voltage is in the TTL logic regime (about 5 volts), so very low power is required.

An alternate approach that can be used when a phase modulator is not available is illustrated in FIGS. 17a and 17b. This self-calibration embodiment measures only the optical signal level of each beam leg, not the dynamic component. The measured values are then combined algebraically to determine the overall normalization factor. The detected photon flux in the two beam legs are multiplied to determine the magnitude of the PEMF response, and a ratio of the two values is obtained to determine the fringe visibility. These two factors are then used to quantify the value of the ultrasonically induced surface vibration. No phase modulation is required to be placed on the beams, and as in the previous embodiment the calibration is performed using the same detectors as are used to detect the acoustic vibrational modulation.

Each detector 169 includes a central PEMF active area 170 within which the gratings 172 are formed, and PEMF electrodes 174 on the opposite sides of the active area parallel to the grating fringes; the same elements are also employed in the detectors 64 of FIGS. 1 and 2. The PEMF electrodes 174 respond to the vibrating fringe pattern to produce the usual non-normalized acoustic vibrational modulation output. In addition, a second set of electrodes 176 is placed on the opposite sides of the PEMF active area on each detector, but perpendicular to the fringes. In these positions the electrodes 176 sense the laser power in each beam. A calibrated value for the acoustic modulation is obtained from the fringe pattern detected by electrodes 174 and the beam powers detected by electrodes 176, as described below.

This dual, paired electrode architecture can be used to detect ultrasonic motion in either direction, if fringes move towards one set of electrodes as opposed to the other set. Or, as an example, if a speckle pattern (without a reference beam) moves in a general direction, then each pair of electrodes would reveal that particular motional component. To distinguish the optical flux in one of the beam legs from the optical flux in the other leg, and thereby enable a proper algebraic processing of the information, a different AC frequency is applied to each leg. One of the optical legs 178, 180 is modulated by reflection off the vibrating workpiece surface (not shown in FIG. 17a) before converging with the other beam at the detector array to form the detector fringe patterns. AC modulations are imposed on the two legs, preferably by conventional electro-optical modulators 182, 184 at different frequencies $\omega 1$ and $\omega 2$ that are displaced from the acoustic frequency but still within the detector's bandwidth. The reference beam chopper can be implemented by the electro-optic modulator 26 or 26a shown in FIG. 1; a similar AC modulator would be placed in the path of the probe beam and operated at a different frequency. The fringe contrast and the total beam power are then algebraically determined by measuring the detected signal at the two frequencies.

The power $P_1$ and $P_2$ in each beam is proportional to the respective signal detected across electrodes 176 at frequencies $\omega_1$ and $\omega_2$ respectively, whereas the absolute value of the fringe contrast $|m|$ is equal to which equals to $$\frac{2\sqrt{P_1 P_2}}{P_1 + P_2},$$

which equals 1 for $P_1=P_2$ and reduces to zero if $P_1$ or $P_2$ equals to zero.

The calculated fringe contrast and total beam power can in turn be used to obtain the calibrated acoustic signal, since the photo-induced current is proportional to the total power detected multiplied by the fringe contrast squared multiplied by the magnitude of the dynamic phase shift between the two beams.

The calculations are preferably performed in the computer 78 for each detector individually, with the results summed together.

To avoid shorting out the photocurrent, the calibration electrodes 176 cannot directly overlap the fringe pattern. This potential problem is circumvented by masking a small region at the ends of the fringe pattern to prevent the fringes from reaching the calibration electrodes. The AC modulations imposed on both of the beam legs causes the fringe pattern to be capacitively coupled into the calibration electrodes 176. Since the length of the fringes, and hence their proximity to the calibration electrodes, varies with the beam powers, the degree of capacitive coupling between the fringes and the calibration electrodes will also vary with the beam powers. Note that in FIG. 17a the processing circuitry 186 is indicated as being integrated onto the same substrate as the detectors.

As described above, each photo-emf element has 2 pairs of opposing electrodes: one pair provides the photo-emf signal, whereas the other pair is used to establish absolute calibration of that given element. In another embodiment that can be realized using the same electrode configuration, each pair of electrodes forms its own ultrasonic sensor; one pair senses ultrasonic motion of a fringe pattern (or other globally moving pattern, such as a speckle pattern) toward the electrodes, whereas the other pair of opposing electrodes can detect motion in a direction towards it (i.e., perpendicular to the first electrodes). In this way, a general motion of the fringes can be resolved into its respective components. As an example, if an object is vibrating laterally along some arbitrary direction in its plane, each pair of electrodes will give a signal output, which is proportional to the vector component along that given direction. Given this two-dimensional vector decomposition, the overall array of pixels can be either combined in a common processor or can be outputted individually. Therefore, two "modes" of operation can be realized, as in the other embodiments of this invention: (1) a single-frame "phased-array" mode, with two-dimensional decomposition; and (2) a single-frame "imaging" system, also with two-dimensional decomposition.

FIG. 18 illustrates the associated processing circuitry. The calibration electrodes 176 for each detector provide an output to a pair of bandpass filters 188, 190, one of which is tuned to $\omega 1$ and the other to $\omega 2$. The fringe pattern is determined from the PEMF electrodes 174 in the fringe pattern algorithm 192 whose output is applied, together with the outputs of bandpass filters 188 and 190, to the processor 78 which executes the equations given above. A similar process takes place for each of the other detectors, the results of all of which are summed together in a summer whose output represents the normalized acoustic signal.

Figure 19A:
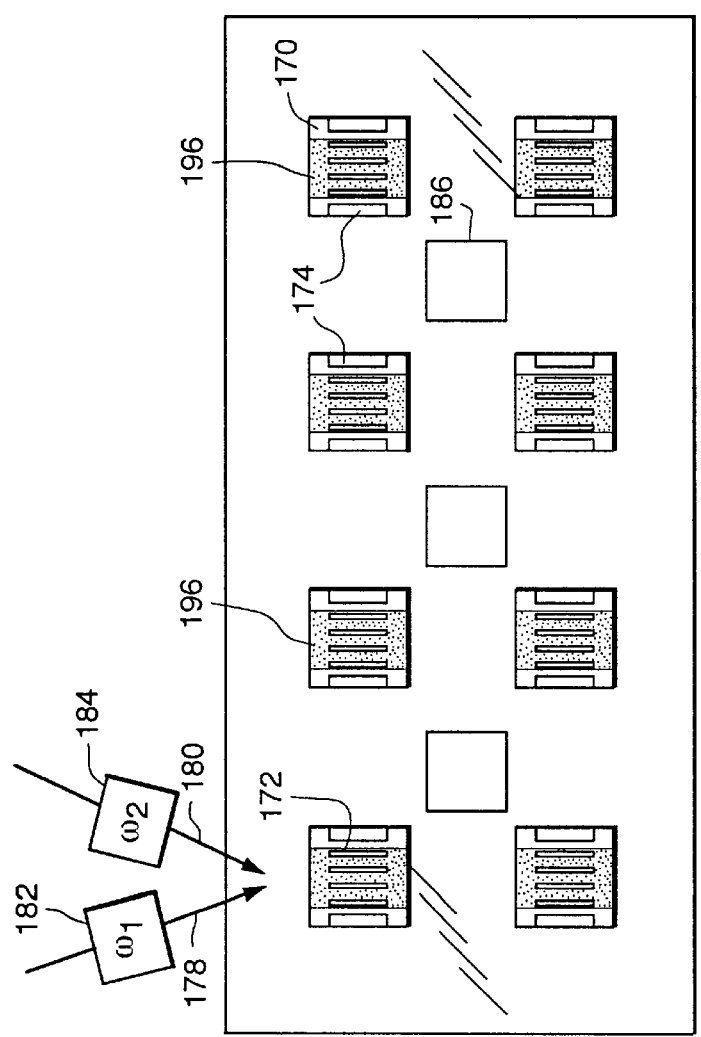
FIGS. 19a and 19b are respectively plan and sectional views of an alternate calibration electrode arrangement with two layers of electrodes.
Figure 19B:
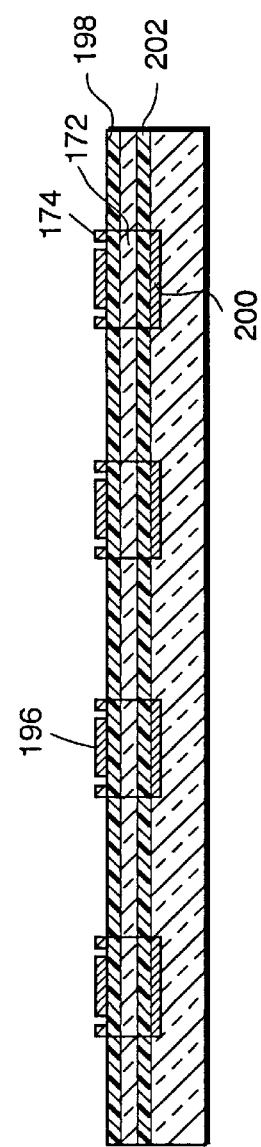

Another embodiment of the photon flux measurement approach is illustrated in FIGS. 19a and 19b. In this embodiment the NSSPEMF detector active areas 170 and the fringe motion sensing electrodes 174 are set up as before. However, instead of the second set of electrodes 176 perpendicular to the fringes, a different set of electrodes is used to "sandwich" the detector active area. The new set of electrodes for each detector consists of a transparent electrode 196, preferably formed from indium tin oxide (ITO), placed over the active area 170 and separated there-from by an insulating layer 198 to prevent electrically shorting out the desired PEMF signal, and another electrode 200 located underneath the active PEMF layer and separated from the active layer by another insulating layer 202. The ITO layer thickness can be chosen so that the upper electrodes also function as antireflection coatings to efficiently couple photons into the detectors for high shot-noise limited performance (subject to the necessity for a minimum conductance to efficiently collect charge at a high enough rate). For each detector, the net photo-signal measured will be a spatial average across the entire detector area. A dual-frequency modulation scheme is again required to distinguish the flux in the two beam legs from each other.

For both the FIGS. 17a, 17b and FIGS. 19a, 19b embodiments, the electrode structure can be easily integrated into the detector structure. This yields a monolithic detector package with on-board processing for each detector element.

In both of the basic approaches described above—the dynamic phase-modulated referencing approach and the photon flux photo detection referencing scheme—the normalization sensing operation can be accomplished either continuously (even prior to or during the acoustic ultrasound measurement), or it can be gated or multiplexed, depending upon the time constants of the given application and the cost versus performance of the on-board processors. In fact, for the reference-beam interferometer, the existing electrode pair on each detector can simply be used to determine the local intensity by gating off the plane-wave reference beam, since typically only the probe beam but not the reference beam will vary in amplitude; the reference beam amplitude can be measured with a separate detector if necessary. Moreover, the photon-flux photo detection system can also be utilized as a system transducer to flag laser power drifts or loss of a threshold signal level to meet the system sensitivity requirements.

Another embodiment of the photo-emf array detector is perform real-time two-dimensional ultrasonic imaging of a surface. In this mode of operation, the signal output from each individual photo-emf element is processed separately relative to all other pixels (recall that, in the other embodiments, the signals from the ensemble are processed collectively to realize a phased-array class of joint detection system). By processing the elements separately, one can view the output signals as "pixels", in a manner similar to a video camera. However, in this case, each pixel yields information regarding surface displacement (or global pattern motion) within the field-of-view of that given pixel. Viewed as a whole, the result is an "image" of the over surface (ultrasonic) displacement of the object under test. In this manner, a ultrasonic mapping of the surface can be obtained in a single frame, without having to raster-scan a probe beam across each resolvable pixel on the surface. The prior art may have implied the possibility of using an array of ultrasonic sensors to simultaneously view a surface. However, the prior art did not reveal a method by which this can be done in a practical manner. For example, an array of Fabry-Perot optical cavities can be, in principle, used to perform this function. However, given the bulky size (one meter cavities), complexity (e.g., servo-controlled cavity biasing), and cost (currently about $70,000 per cavity), realizing an array of even 100 elements would be impractical. On the other hand, using the present invention, an array of 1,000 of the photo-emf sensors can be monolithically formed on a lightweight, single wafer or substrate (for example 7.6 cm in diameter), which can be held in a hand. Moreover, since the photo-emf mechanism is self-stabilizing, no servo-control stabilization system is required (all other interferometers require such stabilization). The array can be in the form of a circular pattern (such as FIG. 1), or in the form of a linear, two-dimensional array (such as FIG. 17a), with each photo-emf element (with its corresponding amplifier, etc.) outputted separately.

While several different embodiments of the invention have been shown and described, numerous variations and alternate embodiments will occur to those skilled in the art. Such variations and alternate embodiment are contemplated, and can be made without departing from the spirit and scope of the invention as defined in the appended claims.

We claim:

1. A contactless sensing system for locating an acoustic source within a medium that has a surface which vibrates in response to acoustic signals from the source, comprising:
    an array of discrete optical detectors,
    a probe beam director for directing an optical probe beam onto said vibrating surface in a pattern that corresponds to said detector array, and for directing at least a portion of the probe beam reflected from said surface onto said detector array,
    a reference beam director for directing a reference beam onto said detector array at an angle to said probe beam to produce fringe patterns on said detectors which correspond to the vibrations along said surface pattern, and
    a readout system that obtains output signals from said discrete detectors to produce an array output signal indicative of at least a two-dimensional location for said acoustic source relative to said surface.

2. The contactless sensing system of claim 1, wherein said optical detectors are non-steady-state photo-induced emf detectors.

3. The contactless sensing system of claim 1, wherein said readout system includes a signal combiner that combines signals from said discrete detectors in producing said array output signal.

4. The contactless sensing system of claim 3, wherein said detectors are arranged in an annular array.

5. The contactless sensing system of claim 4, wherein said annular array is circular.

6. The contactless sensing system of claim 3, further comprising a scanner for scanning said probe beam relative to said surface so that said readout system produces a peak array output signal when said probe beam is aligned with said acoustic source.

7. The contactless sensing system of claim 6, wherein said probe and reference beams include multiple corresponding wavelengths, and said readout system combines signals from said detectors over said wavelengths.

8. The contactless sensing system of claim 7, wherein said signal combiner produces discrete outputs corresponding to said wavelengths, and said readout system includes a computer that combines said signal combiner outputs into a single array output signal.

9. The contactless sensing system of claim 8, said readout system including a width-of-peak detector that detects the width of said peak array output signal as an indication of the acoustic source's depth below said surface.

10. The contactless sensing system of claim 6, said readout system further comprising time gates that, in response to said probe and reference beams being pulsed at a predetermined pulse repetition rate and for predetermined pulse durations, pass said peak array output signal but reject side lobes of said peak signal.

11. The contactless sensing system of claim 6, further comprising analog-to-digital conversion circuitry connected to convert analog signal outputs from said detectors into a digital format, and a computer programmed and connected to add progressively varying sets of phase shifts to said digitally formatted detector outputs to simulate said scanning and to implement said signal combiner by summing said digitally formatted detector outputs for different sets of said phase shifts.

12. The contactless sensing system of claim 11, said computer being programmed to simulate time gates that, in response to said probe and reference beams being pulsed at a predetermined pulse repetition rate and for predetermined pulse durations, pass signals that arrive at said detectors at times that correspond to a given simulated scan location, and reject signals that arrive at said detectors at other times, so that said summing yields a peak signal that corresponds to the location of said acoustic source but rejects side lobes of said peak signal.

13. The contactless sensing system of claim 6, wherein said readout system is arranged to obtain output signals from said detectors only during time intervals that vary for each detector in accordance with the distance between the detector and the scan location on said vibrating surface.

14. The contactless sensing system of claim 3, wherein said detectors are arranged in an annular array, said probe beam director directs an exterior portion of a source optical beam as said probe beam onto said vibrating surface in an annular pattern that corresponds to said annular detector array, and said reference beam director diverts an interior portion of said source beam as said reference beam prior to its reaching said surface.

15. The contactless sensing system of claim 14, wherein said probe and reference beam directors restore said reference beam to a position interior to said probe beam after said probe beam has been directed onto said vibrating surface, and include a common lens in the path of said probe and restored reference beams, said lens having a lens body with an optical axis, a rear surface on said lens body for receiving said probe and restored reference beams, and a front surface on said body that includes inner and outer portions respectively located to receive said restored reference and probe beams transmitted through the lens from its near surface, said outer portion being inclined forward at a greater angle to the lens axis than said inner portion so that said probe beam is refracted by a lesser angle at said outer portion than is said restored reference beam at said inner portion, said inner and outer lens surface portions having an angle between them which causes said probe and reference beams to converge and overlap at a non-zero angle at said detector array.

16. The contactless sensing system of claim 1, further comprising a calibration modulator arranged to establish a relative modulation between at least one of said probe and reference beams and said detector with a calibration signal so that said detector fringe patterns also correspond to said calibration signal modulation, and wherein said readout system is also connected to extract from said detector fringe patterns respective normalization signals representative of said calibration signal, and to use said normalization signals to produce a normalized array output signal.

17. The contactless sensing system of claim 16, wherein said readout system provides normalized outputs from each of said detectors as the magnitudes of their detected vibrations divided by the magnitude of their normalization signals.

18. The contactless sensing system of claim 16, for a surface vibration within a predetermined frequency band, wherein said calibration modulator provides said calibration signal within a frequency band that is separate from said vibration frequency band but still within a frequency response range of said detectors.

19. The contactless sensing system of claim 16, wherein said calibration modulator modulates one of said beams with said calibration signal.

20. The contactless sensing system of claim 16, wherein said probe and reference beam directors direct said probe and reference beams as a common beam onto said vibrating surface and divide said common beam after reflection from said surface.

21. The contactless sensing system of claim 1, wherein said readout system includes a conductive ring surrounding said detector array, with outputs from said detectors coupled to said annular ring and said ring combining said outputs.

22. The contactless sensing system of claim 21, wherein said detector outputs are coupled to said combiner ring through respective amplifiers.

23. The contactless sensing system of claim 22, wherein said detector outputs are coupled to said combiner ring through respective signal processors.

24. The contactless sensing system of claim 21, wherein said detectors are arranged in an annular array within said conductive ring.

25. The contactless sensing system of claim 1, wherein said detectors each comprise two respective pairs of spaced electrodes, with the electrodes of each pair orthogonal to the electrodes of the other pair.

26. A self-calibrating acoustic vibration sensing system, comprising:
   an optical probe system that establishes optical probe and reference beams with at least said probe beam directed to be vibrationally modulated,
   an optical detector, said optical probe system directing said beams onto said detector to form a fringe pattern that corresponds to said vibrational modulation,
   a calibration modulator arranged to establish a relative modulation between at least one of said beams and said detector with a calibration signal so that said fringe pattern also corresponds to said calibration signal modulation, and
   a readout system connected to extract from said fringe pattern a normalization signal representative of said calibration signal, and to use said normalization signal to provide an output signal which represents a normalized value of said vibrational modulation.

27. The system of claim 26, wherein said readout system provides said normalized output signal as the magnitude of said vibrational modulation divided by the magnitude of said normalization signal.

28. The system of claim 26, for a vibrational modulation within a predetermined frequency band, wherein said calibration modulator provides said calibration signal within a frequency band that is separate from said vibrational modulation frequency band but still within a frequency response range of said detector.

29. The system of claim 26, wherein said readout system provides said output signal based upon movement of said fringe pattern.

30. The system of claim 26, wherein said optical detector comprises a non-steady-state photo-induced emf detector.

31. The system of claim 26, wherein said calibration modulator modulates one of said beams with said calibration signal.

32. The system of claim 31, wherein said calibration modulator modulates said probe beam.

33. The system of claim 31, wherein said calibration modulator modulates said reference beam.

34. The system of claim 26, wherein said optical probe system directs only one of said beams to be vibrationally modulated.

35. The system of claim 26, wherein said optical probe system directs both of said beams to be vibrationally modulated.

36. The system of claim 35, wherein said optical probe system establishes a common beam, directs it to be vibrationally modulated, and divides said common beam into said probe and reference beams after the beam has acquired a vibrational modulation, further comprising a time delay that delays said reference beam before it reaches said detector so that said fringe pattern is formed between said probe beam and a time delayed replica of itself.

37. The system of claim 26, wherein said calibration modulator modulates at least one of said beams by amplitude modulation at a predetermined frequency.

38. The system of claim 37, wherein said calibration modulator amplitude modulates each of said beams at different respective frequencies.

39. The system of claim 38, said detector including first and second sets of electrodes arranged to respectively detect said vibrational and calibration modulations, with said first set of electrodes substantially parallel to said fringe pattern and said second set of electrodes capacitively coupled to sense said calibration modulation from said fringe pattern.

40. The system of claim 39, wherein said first and second sets of electrodes are substantially coplanar, and said second set of electrodes is substantially orthogonal and capacitively coupled to said fringe pattern.

41. The system of claim 39, wherein said second set of electrodes comprise a first transparent electrode and a second electrode that are respectively disposed above and below and capacitively coupled to said fringe pattern.

42. The system of claim 26, wherein said calibration modulator modulates the position of said detector relative to said beams with said calibration signal.

43. A contactless sensing system for locating an acoustic source within a medium that has a surface which vibrates in response to acoustic signals from the source, comprising:
   an annular array of discrete optical detectors,
   an optical probe system that optically probes locations on a vibrating surface that correspond to the locations of said detectors in said annular array, and optically induces outputs from said detectors that vary in accordance with the vibrations at their corresponding locations on the surface, and
   a scanner that scans said optical probing relative to a surface being probed.

44. The contactless sensing system of claim 43, further comprising a signal combiner that combines signals from said discrete optical detectors to produce an array output signal.

45. The contactless sensing system of claim 44, said signal combiner comprising a conductive ring around said detector array, with the outputs of said detectors coupled to said ring.

46. The contactless sensing system of claim 45, wherein said detector outputs are coupled to said combiner ring through respective amplifiers.

47. The contactless sensing system of claim 45, wherein said detector outputs are coupled to said combiner ring through respective signal processors.

48. The contactless sensing system of claim 43, wherein said scanner causes a mechanical scanning of said optical probing relative to the probed surface.

49. The contactless sensing system of claim 43, wherein said scanner simulates a mechanical scanning by phased array scanning of said detector array relative to the probed surface.

50. The contactless sensing system of claim 43, wherein said scanner simulates a mechanical scanning by time gated scanning of said detector array relative to the probed surface.

51. The contactless sensing system of claim 43, wherein said optical probe system establishes optical probe and reference beams with at least said probe beam directed to be vibrationally modulated by said vibrating surface, and directs said beams onto said detectors to form fringe patterns that correspond to said vibrational modulation; further comprising a calibration modulator arranged to establish a relative modulation between at least one of said beams and said detector with a calibration signal so that said fringe patterns also correspond to said calibration signal modulation, and a readout system connected to extract from said fringe patterns a normalization signal representative of said calibration signal, and to use said normalization signal to provide an output signal which represents a normalized value of said vibrational modulation.

52. The contactless sensing system of claim 51, wherein said readout system provides said normalized output signal as the magnitude of said vibrational modulation divided by the magnitude of said normalization signal.

53. The contactless sensing of claim 51, for a vibrational modulation within a predetermined frequency band, wherein said calibration modulator provides said calibration signal within a frequency band that is separate from said vibrational modulation frequency band but still within a frequency response range of said detectors.

54. The contactless sensing system of claim 51, wherein said calibration modulator modulates one of said beams with said calibration signal.

55. The contactless sensing system of claim 54, wherein said optical probe system directs both of said beams to be vibrationally modulated.

56. The contactless sensing system of claim 55, wherein said optical probe system establishes a common beam, directs it to be vibrationally modulated, and divides said common beam into said probe and reference beams after the beam has acquired a vibrational modulation, further comprising a time delay that delays said reference beam before it reaches said detector so that said fringe pattern is formed between said probe beam and a time delayed replica of itself.

57. The contactless sensing system of claim 51, wherein said calibration modulator modulates at least one of said beams by amplitude modulation at a predetermined frequency.

58. The contactless sensing system of claim 57, wherein said calibration modulator amplitude modulates each of said beams at different respective frequencies.

59. The contactless sensing system of claim 58, wherein said readout system includes a computational element that computes said output signal from the equation.

60. The contactless sensing system of claim 51, wherein said calibration modulator modulates the position of said detector relative to said beams with said calibration signal.

* * * * *